United States Patent [19]

Durst et al.

[11] Patent Number: 5,756,362
[45] Date of Patent: May 26, 1998

[54] LIPOSOME-ENHANCED IMMUNOAGGREGATION ASSAY AND TEST DEVICE

[75] Inventors: Richard Allen Durst, Romulus, N.Y.; Matthew A. Roberts, Olney, Md.

[73] Assignee: Cornell Research Foundation, Inc., Ithaca, N.Y.

[21] Appl. No.: 382,482

[22] Filed: Feb. 1, 1995

Related U.S. Application Data

[63] Continuation-in-part of Ser. No. 135,741, Oct. 12, 1993.
[51] Int. Cl.$^6$ .................. G01N 33/543; G01N 33/558
[52] U.S. Cl. .................. 436/518; 422/56; 422/58;
435/7.5; 435/287.1; 435/287.2; 435/287.7;
435/287.9; 435/805; 435/810; 435/970;
436/169; 436/164; 436/172; 436/514; 436/528;
436/530; 436/533; 436/534; 436/536; 436/538;
436/541; 436/800; 436/805; 436/807; 436/810;
436/815
[58] Field of Search .................. 422/56–58; 435/7.5,
435/287.1, 287.2, 287.7, 287.9, 805, 810,
970; 436/514, 518, 528, 530, 533, 534,
536, 538, 541, 169, 172, 800, 164, 805,
807, 810, 815, 829, 901

[56] References Cited

U.S. PATENT DOCUMENTS

| | | | |
|---|---|---|---|
| 4,048,298 | 9/1977 | Niswender | 424/12 |
| 4,235,601 | 11/1980 | Deutsch et al. | |
| 4,517,288 | 5/1985 | Giegel et al. | |
| 4,517,303 | 5/1985 | Freytag et al. | |

(List continued on next page.)

FOREIGN PATENT DOCUMENTS 2-204398  11/1988  United Kingdom.

OTHER PUBLICATIONS

Locascio–Brown, et al., Liposome Flow Injection Immunoassay: Implications for Sensitivity, Dynamic Range, and Antibody Regeneration, *Analytical Chemistry*, pp. 2587–2593 (Dec. 1, 1990).

(List continued on next page.)

*Primary Examiner*—Christopher L. Chin
*Attorney, Agent, or Firm*—Nixon, Hargrave, Devans & Doyle

[57] ABSTRACT

A test device for detecting or quantifying an analyte in a test sample includes an absorbent material having separate contact and measurement portions. The contact portion is positioned at or proximate to a first end of the absorbent material. The measurement portion has a receptor for a conjugate of an analyte analog and marker-encapsulating liposomes. In a method for using the test device, a binding material specific for the analyte is combined with the liposome-analyte analog conjugate and the test sample to form a test mixture. The mixture is incubated for a time sufficient to permit competition between any analyte present and the conjugate for the binding material. Following incubation, the mixture is allowed to traverse the absorbent material from the contact portion through the measurement portion of the absorbent material. Following traversal by the test mixture, the presence or amount of marker in the measurement portion of the absorbent material is then detected and correlated with the presence or amount, respectively, of the analyte in the sample.

Liposomes encapsulating an electroactive marker are used in conjunction with a test device as described above but which includes an electrochemical measurement portion in place of the measurement portion described above. Test devices and methods employing electrochemical detection or quantification of an electroactive marker corresponding to the amount of analyte in a sample may be either amperometric or potentiometric.

18 Claims, 13 Drawing Sheets

U.S. PATENT DOCUMENTS

| | | |
|---|---|---|
| 4,594,327 | 6/1986 | Zuk . |
| 4,636,479 | 1/1987 | Martin et al. . |
| 4,668,619 | 5/1987 | Greenquist et al. . |
| 4,703,017 | 10/1987 | Campbell et al. . |
| 4,752,572 | 6/1988 | Sundberg et al. . |
| 4,806,311 | 2/1989 | Greenquist . |
| 4,874,710 | 10/1989 | Piran . |
| 4,916,080 | 4/1990 | Imai et al. . |
| 4,920,046 | 4/1990 | McFarland et al. . |
| 4,939,098 | 7/1990 | Suzuki et al. . |
| 5,006,473 | 4/1991 | Bouma et al. . |
| 5,081,013 | 1/1992 | Rovelli et al. . |
| 5,085,987 | 2/1992 | Olson . |
| 5,096,629 | 3/1992 | Nanba et al. . |
| 5,141,751 | 8/1992 | Tomikawa et al. . |
| 5,308,775 | 5/1994 | Donovan et al. . |
| 5,310,650 | 5/1994 | McMahon et al. . |

OTHER PUBLICATIONS

Yap, et al., Liposome Flow Injection Immunoassay: Model Calculations of Competitive Immunoreactions Involving Univalent and Multivalent Ligands, *Analytical Chemistry*, 63:2007-11 (Sep. 15, 1991).

Durst, et al., Automated Liposome-Based Flow Injection Immunoassay System, GBF (Gesellschaft für Biotechnologische Forschung) Monographs, vol. 14, pp. 181-190 (1990).

Zuk, et al., Enzyme Immunochromatography-A Quantitative Immunoassay Requiring no Instrumentation, *Clin. Chem.*, 31:7, 1144-50 (1985).

Durst, et al., *Chemically Modified Electrode for Liposome--Mediated Homogeneous Immunoassay*, 5th Symposium on Ion-Selective Electrodes, Pergamon Press, Oxford (1989).

Armbruster, et al., Screening for Drugs of Abuse with the Roche ONTRAK Assays, *J. Anal. Tox.*, vol. 16, pp. 172-175 (May/Jun. 1992).

Losso, et al., Development of a Particle Concentration Fluorescence Immunoassay for the Quantitative Determination of IgG in Bovine Milk, *J. Agric. Food Chem.*, vol. 41, pp. 682-686 (1993).

Rosenzweig, et al., Laser-Based Particle-Counting Microimmunoassay for the Analysis of Single Human Erythrocytes, *Anal. Chem.*, vol. 66, pp. 1771-1776 (1994).

Collard-Bovy, C., et al., Microparticle-Enhanced Nephelometric Immunoassay. 1. Measurement of $\alpha_s$-Casein and κ-Casein, *J. Dairy Sci.*, vol. 74, pp. 3695-3701 (1991).

Heath-Fracica, et al., Evaluation of a New Latex Agglutination Test for Detection of Streptococcal Antibodies, *Diagn. Microbiol. Infect. Dis.*, vol. 8, pp. 25-30 (1987).

Pinnaduwage, et al., Stable Target-Sensitive Immunoliposomes, *Biochemistry*, vol. 31, pp. 2850-2855 (1992).

Babbitt, et al., Contact-Dependent, Immunecomplex-Mediated Lysis of Hapten-Sensitized Liposomes, *Bioconjugate Chem.*, vol. 4, pp. 199-205 (1993).

Lou, et al., One-Step Competitive Immunochromatographic Assay for Semiquantitative Determination of Lipoprotein(a) in Plasma, *Clin. Chem.*, vol. 39, pp. 619-624 (1993).

Allen, et al., A Noninstrumented Quantitative Test System and Its Application for Determining Cholesterol Concentration in Whole Blood, *Clin. Chem.*, vol. 36, pp. 1591-1597 (1990).

Plant, et al., Generic Liposome Reagent for Immunoassays, *Anal. Biochem.*, vol. 176, pp. 420-426 (1989).

Monroe, Novel Liposome Immunoassays for Detecting Antigens, Antibodies and Haptens, *J. Liposome Res.*, vol. 1, pp. 339-377 (1989-90).

Parsons et al., "Multianalyte Assay System Developed for Drugs of Abuse, " *Clin. Chem.*, 39:1899-1903 (1993).

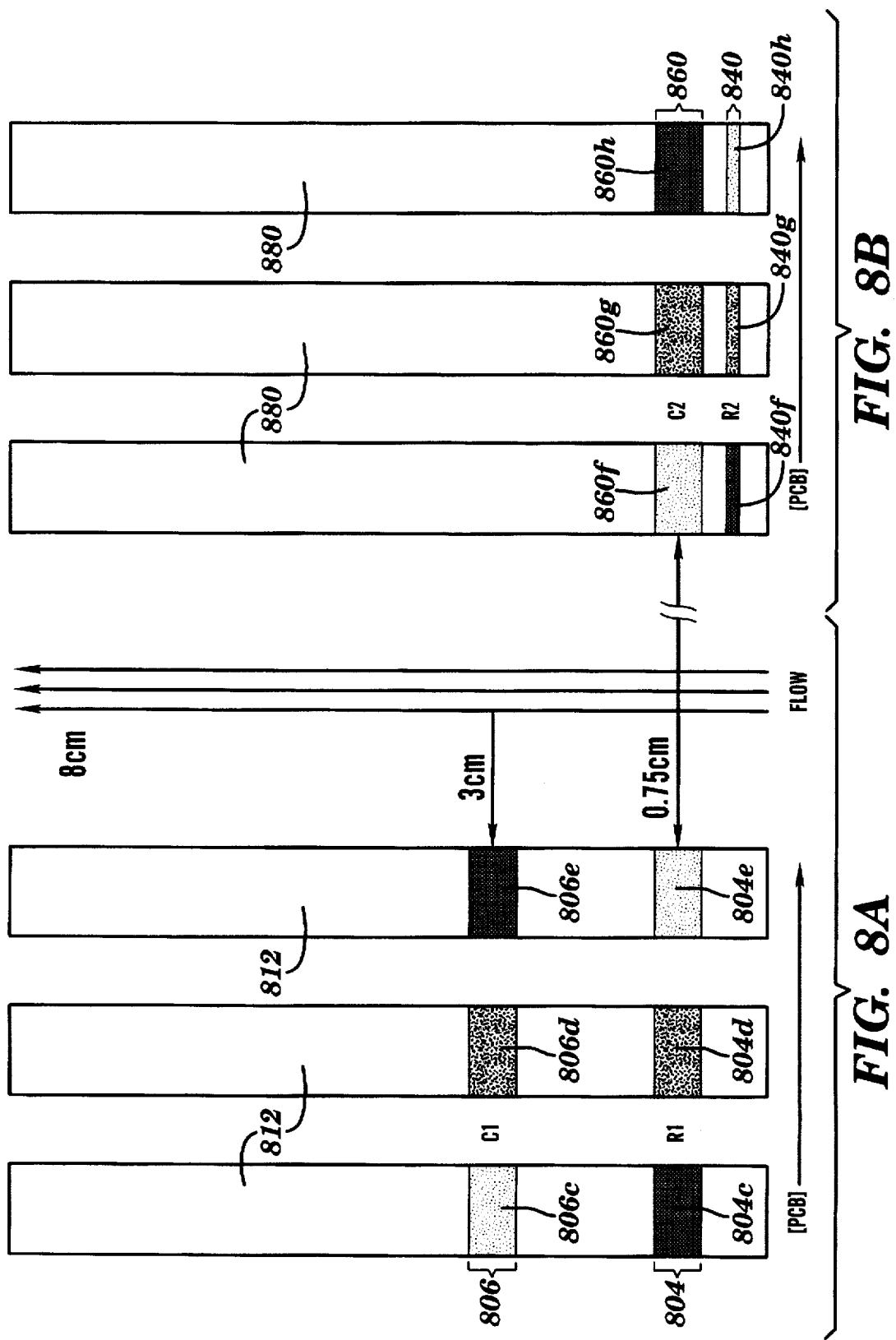

5,756,362

LIPOSOME-ENHANCED IMMUNOAGGREGATION ASSAY AND TEST DEVICE

CROSS-REFERENCE TO RELATED APPLICATION

This application is a continuation-in-part of Ser. No. 08/135,741, filed Oct. 12, 1993.

This study was partially funded by the National Institutes of Health, DHHS, under the Superfund Basic Research and Education Program, NIEHS ES-05950.

FIELD OF THE INVENTION

The present invention relates to a method for detecting or determining one or more analytes, and a test device used in the method. More particularly, the invention relates to a single-use test strip for use in an immunomigration assay employing marker-loaded liposomes for signal amplification.

BACKGROUND OF THE INVENTION

There is an increasing need for rapid, reliable, and inexpensive methods for detecting and measuring pollutants and contaminants in the environment and in food sources. Conventional analytical methods such as high pressure liquid chromatography, gas chromatography/mass spectroscopy, atomic absorption spectroscopy, etc. are particularly unsuitable for use in the field, because such methods are generally complex and employ instruments and equipment which are expensive and susceptible to damage from transport and possible contamination in the field. Gathering samples in the field for analysis at a remote laboratory is similarly unsatisfactory, because it may take a few days to several weeks from sample acquisition to obtain the results.

The need for simple, rapid, and inexpensive field assays has led to an investigation of immunoassays for surveying environmental contamination. Polychlorinated biphenyls (PCBs), for example, which were sold commercially in the United States-under the Aroclor trademark, were industrial compounds used extensively as lubricants, fire retardants, immersion oils, dielectric and heat transfer fluids, as well as a multitude of other products. Safe, S. *Toxicology* 1990, 3, 51–88. They have been contaminated an enormous variety of media, primarily as a result of careless use, disposal, and accidents, and have now been identified by the EPA as priority pollutants to be targeted for remediation under the national Superfund program. Extensive efforts have recently been undertaken to characterize Superfund sites by both the EPA and various environmental remediation firms. One of the chief obstacles to the prompt completion of such studies is the high cost and long turnaround time for conventional PCB analysis by off-site laboratories.

Immunoassays comprise one category of specific binding assays, which generally rely on the affinity of naturally occurring receptors or antibodies for specific compounds. The specific binding pairs employed in immunoassays are either an antigen or a hapten, and the antibody produced in an immune response to the antigen or hapten.

Competitive immunoassays are generally based upon the competition between a specific analyte, the amount of which is to be determined, and a labelled form of the analyte or an appropriate analog thereof, which is used as an indicator, for a limited number of available binding sites on a binding material specific for the analyte. Using a known amount of the labelled analyte, the amount of analyte in the sample can be determined by measuring the amount of the unbound labelled analyte, which in some systems is physically separated from the bound indicator during the assay. Alternatively, where it is possible to distinguish bound from unbound indicator, such as where detectable physical or chemical changes in the indicator occur as a result of the binding reaction, an assay can be completed without separating the bound and unbound indicator.

The types of materials commonly used as immunoassay label materials or markers include various enzymes, fluorescent dyes, chemiluminescent reactants, and radioisotopes. Such materials are often conjugated to the analyte, as in the case of enzymes and radioisotopes, or less frequently, carried within sacs such as animal erythrocytes, polymer microcapsules, or liposomes.

Immunoassays have been widely used for medical diagnosis for many years. More recently, immunoassays have been more broadly applied for the determination of toxic substances in the environment and in food. Practical applications for immunoassays in environmental analysis include evaluating the geographical scope and magnitude of pollutants, monitoring the fate and persistence of contaminants, and assessing the effectiveness of remediation efforts. Raw and processed foods must similarly be tested for chemical and biological contamination.

A wide variety of immunoassays, reagents, and test devices which exploit the interaction between the members of specific binding pairs to detect or measure a substance in a test sample have been developed. Sophisticated, automated immunoassay systems are successfully employed in laboratory settings, but there are also many types of portable sensing devices which can be used outside the laboratory. Some portable immunoassays and test devices have even been developed for use in the home by untrained individuals. Home pregnancy test kits are an example of such immunoassay test kits.

Immunoassay techniques have shown considerable promise for the characterization of PCB contamination. Most assays have chosen the ELISA (enzyme-linked immunosorbent assay) format which is often based on the competition between sample analyte and analyte-enzyme conjugates for a limited number of antibody binding sites. These methods offer many advantages such as speed, minimal sample cleanup, and high sensitivity and selectivity over standard laboratory techniques. Kaufman, B. M.; Clower, M. J. Assoc. Off. Anal. Chem. 1991, 74, 239–247. Van Vunakis, H. In *Immunochemical methods for environmental analysis;* Van Emon, J. M.; Mumma, R. O., Ed.; ACS: Washington, D.C., 1990; Vol. 442; 1–12. Furthermore, the analysis can, in many cases, be conducted in the field, thus reducing the delays and other logistical problems associated with transporting expensive samples to remote laboratories. Mapes, J. P.; McKenzie, K. D.; Stewart, T. N.; McClelland, L. R.; Studabaker, W. B.; Manning, W., B.; Friedman, S. B. Bull. Environ. Contam. Toxicol. 1993, 50, 219–225. However, ELISA tests still involve numerous solution changes, timed reactions, and a whole series of critical steps that can be a source of operator error when conducted in the field, under non-optimal conditions.

Several commercially available on-site ELISA tests have been developed to satisfy the demand for affordable and rapid site characterization for PCB contamination. Mapes, J. P.; McKenzie, K. D.; Stewart, T. N.; McClelland, L. R.; Studabaker, W. B.; Manning, W., B.; Friedman, S. B. Bull. Environ. Contam. Toxicol. 1993, 50, 219–225. Fribush, H. M.; Fisk, J. F. In *Environmental Lab;* 1992; 36–41. Engle, S.

W.; Harrison, R. O.; Scallon, A.; Meckes, M. C. In *Superfund '92*; HMCRI-Hazardous Materials Control Research Institute, Washington, D.C., 1992. These kits are still estimated to cost between $25 and $50 per sample (obtained from the manufacturers' literature) and often require specially trained operators to obtain reproducible results, which introduces higher labor costs. Although this represents a great improvement over conventional analysis there still remains the impetus for the development of increasingly lower cost and easier to use on-site techniques. Hammock, B. D.; Gee, S. J.; Harrison, R. O.; Jung, F.; Goodrow, M. H.; Li, Q.X.; Lucas, A. D.; Szekacs, A.; Sundaram, K. M. S. In *Immunochemical methods for environmental analysis;* J. M. Van Emon and R. O. Mumma, Ed.; American Chemical Society; Washington, D.C., 1990; Vol. 442; 112–139.

An immunochromatographic assay method for whole blood samples is described in U.S. Pat. No. 4,594,327 to Zuk. At least one member of the specific binding pair is uniformly bound to the entire surface of a solid bibulous element. The element is contacted with the whole blood sample containing the analyte in an aqueous medium so that the sample traverses the element to define a border related to the amount of analyte. The analyte concentration is directly related to the distance the analyte has traversed. Zuk further describes determination of the border by a separate development step, such as an enzyme or chromophore signal production and amplification system.

U.S. Pat. No. 5,085,987 to Olson also describes an immunoassay employing a bibulous element such as a piece of paper affixed to plastic with adhesive. The element is contacted with the test solution suspected of containing the analyte, to which has been added an antibody for the analyte and a conjugate of the analyte and a label. The element contains a first receptor for the conjugate which is bound to a situs on the element separated from the contact portion, and a second receptor capable of binding the antibody for the analyte, which is bound to the element between the first receptor and the contact portion. The test solution moves along the element by capillary action. The situs is examined for the presence of conjugate, either by exposing the situs to a signal producing means capable of interacting with the label to produce a signal in a separate development step, such as an enzyme-catalyst-substrate system, or by directly measuring the signal from a radioactive label.

U.S. Pat. No. 4,939,098 to Suzuki, et al. discloses an immunoassay device for simultaneous determination of at least two components in a sample. At least two reagents, each of which reacts specifically with one of the components in the sample, are supported in optional places on development layer. Residual components in the sample which do not react with the reagent first contacted by the sample continue to be moved past the place on the development layer where the first reagent is supported. After the movement of the unreacted components past each of the reagent places, the amount of the two reaction products still held in the development layer are measured. Test reagents may be included in liposomes, which are immobilized on the development layer by physical adsorption or chemical bonding.

In Suzuki, a detectable label substance such as a chelating agent, an enzyme or a fluorescent substance may be enclosed in the liposomes in addition to the antibody or antigen test reagents for qualitative or quantitative analysis of sample components. The liposomes or other label sacs are lysed by the antigen-antibody reaction or complement activity, to release label for detection or quantification. Suzuki further describes an electric measurement method in which the liposomes contain a substance detectable with electrodes. A solution of the liposomes is removed from the development layer, and the amount of the component to be measured is quantified from the amount of signal produced at the electrode.

As a result of the complexity of the device and method described in Suzuki, Suzuki's technique is not well-suited for use in the field, or for use by untrained personnel. High voltage is required for the electrophoretic separation method, for example.

Immunoassays employing liposomes for signal production are described in U.S. Pat. Nos. 4,874,710 to Piran and 4,703,017 to Campbell. In Piran, the sample containing the analyte is contacted with a binder for the analyte in the presence of a conjugate of a ligand coupled to a sac lysing agent. The ligand may be designed to bind either with the analyte or the binder. Unbound conjugate, which includes a sac lysing agent, comes into contact with immobilized liposomes, which release a detectable marker. Signal from the marker is measured in the aqueous assay medium. The binder and sacs may be placed on different portions of a solid support, such as a "dip stick" which may be inserted into and withdrawn from the assay medium.

Campbell discloses an immunoassay for determination of an analyte using a tracer, such as the analyte labelled with liposome-encapsulated markers. The tracer can be visually determined without instrumentation and without further treatment of the tracer (such as sac lysing). A binder for at least one of the analyte and the tracer is supported on a test area of a solid support, which is preferably nitrocellulose in the form of a card, test strip, or dipstick. Detection or quantification of the signal, e.g., color from a dye, is made in the test area of the device. Competitive, sandwich, and inhibition embodiments of the assay are disclosed.

The use of an agglutination-based portable assay, for on-site detection of drugs of abuse, has been reported. Parsons, R. G.; Kowal, R.; LeBlond, D.; Yue, V. T.; Neargarder, L.; Bond, L.; Garcia, D.; Slater, D.; Rogers, P. *Clin. Chem.* 1993, 39, 1899–1903. This system employs a modified hemagglutination inhibition mechanism, using blue-stained Duracytes, that is analyzed with paper chromatography. Duracytes are fixed human erythrocytes. In the method described in Parsons et al., the Duracytes are coated with anti-fluorescein antibody and combined with antisera to five drugs (amphetamines, cannabinoids, cocaine metabolites, opiates, and PCP). The test sample is added to this combination, and the entire mixture (test sample, Duracytes, and antisera) is loaded onto a multichambered vessel device.

The device automatically distributes the mixture into distinct assay channels, each containing different dried flourescein-drug conjugates. Negative assays (no drug present) form an agglutinated reaction product (as a result of reactions between the Duracytes, the conjugate, and the anti-drug antibody), while positive assays show no agglutination. Agglutination results in the production of characteristic banded patterns in the channels showing a negative result.

Parsons et al. thus requires two different antibodies for agglutination, one coated on the Duracytes and one immobilized on a solid surface. In addition, Parsons relies on the production of signal for negative results, which is counterintuitive, and its narrow dynamic range for detection effectively limits its usefulness when quantitation is desired. Also, the range of markers which can be applied to the Duracytes is limited.

In view of the above-noted deficiencies and complexities of prior techniques for use as rapid, reliable, and simple field assays, the need remains for technology which will accurately detect and determine analytes such as environmental and food contaminants.

SUMMARY OF THE INVENTION

The present invention relates to a test device for detecting or quantifying an analyte in a test sample. The test device includes an absorbent material, having a contact portion at or proximate to one end. A measurement portion is positioned away from the first end of the absorbent material. The measurement portion has a receptor for a conjugate of an analog of the analyte to be determined and liposomes comprising a detectable marker.

The present invention further provides a method for detecting or quantifying an analyte in a test sample utilizing the test device of the invention. The test sample is combined with a binding material specific for the analyte, and a conjugate of an analyte analog and liposomes comprising a detectable marker, to form a mixture. The mixture is incubated for a time sufficient to allow competition between the conjugate and any analyte present for the binding material. The mixture is then contacted with the contact portion at or proximate to one end of the absorbent material of the test device. The test mixture is allowed to traverse the absorbent material, via capillary action, from the contact portion through a measurement portion of the absorbent material which is positioned away from the end to which the contact portion is at or proximate. The measurement portion has a receptor for the analyte analog-liposome conjugate. After the test mixture has traversed the absorbent material of the test device as described above, the presence or amount of marker in the measurement portion of the absorbent material is detected and correlated with the presence or amount, respectively, of the analyte in the sample.

The invention further provides a method and device for detecting or quantifying an analyte in a test sample employing an automatic electrochemical signal production and amplification method. In this aspect, the test device comprises an absorbent material, having a contact portion as described above. However, the measurement portion described above is replaced in this embodiment with an electrochemical measurement portion. The electrochemical measurement portion may be designed for either amperometric or potentiometric measurement.

For amperometric measurement, the electrochemical measurement portion has working, reference, and counter electrode portions, each of which is segregated from each other and from the contact portion on the absorbent material. The working, reference, and counter electrodes are adapted for electrical connection with one another through an appropriate electrochemical analyzer. A liposome lysing agent is also bound to the absorbent material, either in the working electrode portion, or in a liposome lysing portion positioned between the contact portion and the working electrode portion, and segregated from the contact portion.

The present invention further provides a method for detecting or quantifying an analyte in a test sample utilizing a test device which relies on electrochemical detection of an electroactive marker. The test sample is combined with a binding material specific for the analyte, and a conjugate of an analyte analog and liposomes comprising an electroactive marker, in an electrolyte mixture. The electrolyte mixture is then incubated for a time sufficient to permit competition between the conjugate and the analyte, if present, for the binding material. Following incubation, the mixture is contacted with a contact portion at or proximate to one end of the absorbent material of the test device. The test mixture is allowed to traverse the absorbent material, via capillary action, from the contact portion through an electrochemical measurement portion of the absorbent material which is positioned away from the end to which the contact portion is proximate. The electrochemical measurement portion includes working, reference, and counter electrode portions, adapted for electrical connection with one another, and segregated from each other and from the contact portion on the absorbent material. The absorbent material further has a liposome lysing agent bound to the absorbent material, either in the working electrode portion, or in a liposome lysing portion position between the portion and the working electrode portion. The liposome lysing portion is segregated from the contact portion. As the test mixture traverses the absorbent material of the test device as described above, the flow of electrolyte test mixture through or across the working electrode and reference electrode portions and into the counter electrode portion completes a circuit between the counter and working electrode portions, causing current to flow. Also, the liposomes come into contact with the liposome lysing agent, and lysis of the liposomes causes release of the electroactive marker. The presence or amount of current flowing between the counter and working electrode portions is then detected, and correlated with the presence or amount, respectfully, of the analyte in the sample.

A test device designed for potentiometric marker measurement is also provided in accordance with the invention. This test device is as described above, except that the electrochemical measurement portion has indicator electrode and reference electrode portions adapted for electrical contact with one another, wherein the indicator electrode portion is positioned between and segregated from the contact portion and from the reference electrode on the absorbent material. A liposome lysing agent is also bound to the absorbent material, either in the indicator electrode portion, or in a liposome lysing portion which is positioned between the contact portion and the indicator electrode portion, and which is segregated from the contact portion.

A method for detecting or quantifying an analyte using such a test device is also provided in accordance with the invention. As before, an electrolyte mixture containing the analyte and a conjugate of analyte analog and liposomes comprising an electroactive marker, and a binding material specific for the analyte is incubated for a time sufficient to permit competition between any analyte present and the conjugate for the binding material. Following incubation, the mixture is allowed to traverse the absorbent material from the contact portion through the electroactive measurement portion. As the electrolyte test mixture flows through the indicator electrode portion into the reference electrode portion, a potential differential is set up between the two electrode portions. In addition, the liposomes are lysed by contact with the liposome lysing agent. The presence or amount of potential difference between the two electrodes is then detected and correlated with the presence or amount, respectively, of the analyte in a sample.

The device and method of the invention can be used directly in the field. The device is used only once, and, therefore, is free from residual environmental contaminants other than what may be present in the sample to be measured. Samples can be assayed within minutes after collection, with the results immediately available on-site. In addition, the device and method of the invention are much less complex than many of the prior materials and methods. For example, a visible dye can be used as the detectable marker, eliminating the need for any detection or measurement instrumentation, and a separate marker or indicator development step is not required with any embodiment of the invention. Also, marker-loaded liposomes as used in the device and method of the invention provide a highly sensitive, rapid or even instantaneous signal production/ amplification system. Furthermore, the amount of marker measured in the measurement portion of the absorbent material of the test device is directly proportional to the analyte concentration in the sample. This feature of the invention provides a particular advantage over prior test devices and immunoassays, providing an intuitive correlation between signal strength and analyte concentration.

BRIEF DESCRIPTION OF THE DRAWINGS

FIG. 8 is a side-by-side schematic comparison of test devices in accordance with the invention described in copending application Ser. No. 08/135,741 (FIG. 8A) and test devices in accordance with the invention (FIG. 8B). In each of FIGS. 8A and 8B, the devices are depicted with increasing concentrations of PCEs from left to right.

FIG. 13A illustrates the time-dependent increase in laser light obscuration observed for liposome solutions containing 0 and 100 ppb of Aroclor 1232. FIG. 13B depicts all particle information at each time point, as described in greater detail following the Examples, below. FIG. 13C is a plot of number percentage of large diameter articles vs. time.

DETAILED DESCRIPTION OF THE INVENTION

Figure 1:
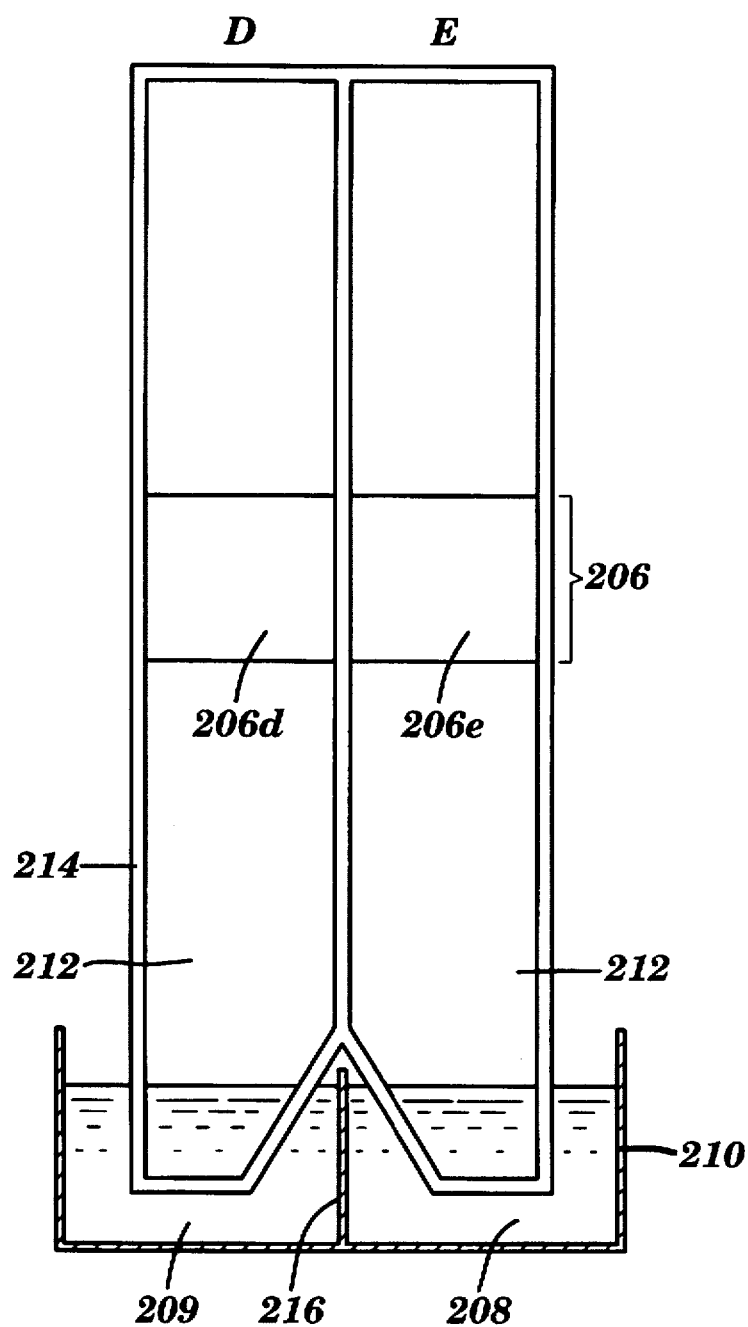
FIG. 1 is a schematic of a multiple channel test device in accordance with the invention.

As described above, the present invention is directed to a test device for detecting or quantifying an analyte in a test sample. The test device includes an absorbent material which comprises a contact portion at or proximate to a first end of the absorbent material. The absorbent material of the test device further comprises a measurement portion at a location on the absorbent material which is positioned away from the first end. The measurement portion has a receptor for a conjugate of an analyte analog and liposomes, wherein the liposomes comprise a detectable marker.

The invention is also directed to a method for detecting or quantifying an analyte, including the steps of providing a test device as described immediately above, combining a binding material specific for the analyte with the conjugate and the test sample to form a mixture, incubating the mixture for a time sufficient to permit competition between the conjugate and the analyte for the binding material, contacting the mixture with the contact portion of the test device after incubation, allowing the mixture to migrate from the contact portion through the measurement portion of the absorbent material, detecting the presence amount of the marker in the measurement portion of the absorbent material and correlating the presence or amount of the marker in the measurement portion with the presence or amount, respectfully, of the analyte in the sample.

The invention further provides a method and device for detecting or quantifying an analyte in a test sample employing an automatic electrochemical signal production and amplification method. In this aspect, the test device comprises an absorbent material, having a contact portion as described above. However, the measurement portion described above is replaced in this embodiment with an electrochemical measurement portion. The electrochemical measurement portion may be designed for either amperometric or potentiometric measurement.

For amperometric measurement, the electrochemical measurement portion has working, reference, and counter electrode portions, each of which is segregated from each other and from the contact portion on the absorbent material. The working, reference, and counter electrodes are adapted for electrical contact with one another. A liposome lysing agent is also bound to the absorbent material, either in the working electrode portion, or in a liposome lysing portion positioned on the absorbent material between the contact portion and the working electrode portion, and segregated from the contact portion.

The present invention further provides a method for detecting or quantifying an analyte in a test sample utilizing a test device which relies on electrochemical (amperometric) detection of an electroactive marker. An electrolyte mixture containing the analyte, a conjugate of an analyte analog and liposomes comprising an electroactive marker, and a binding material specific for the analyte is incubated for a time sufficient to allow the analyte and the conjugate to compete for the binding material. Following the incubation, the electrolyte mixture is contacted with a contact portion proximate to one end of the absorbent material of the test device. The test mixture is allowed to traverse the absorbent material, via capillary action, from the contact portion through an electrochemical measurement portion of the absorbent material which is positioned away from the end to which the contact portion is proximate. The electrochemical measurement portion includes working, reference, and counter electrode portions, which are adapted for electrical connection with one another, and which are segregated from each other and from the other portions on the absorbent material. The absorbent material further has a liposome lysing agent bound to the absorbent material, either on the working electrode portion, or in a liposome lysing portion position between the contact portion and the working electrode portion. The liposome lysing portion is segregated from the contact portion. As the test mixture traverses the absorbent material of the test device as described above, the flow of electrolyte test mixture through or across the working electrode and reference electrode portions and into the counter electrode portion completes a circuit between the counter and working electrode portions, causing current to flow. Also, the liposomes come into contact with the liposome lysing agent, and lysis of the liposomes causes release of the electroactive marker. The presence or amount of current flowing between the counter and working electrode portions is then detected and correlated with the presence or amount of the analyte in the sample.

A test device designed for potentiometric marker measurement is also provided in accordance with the invention. This test device is as described above, except that the electrochemical measurement portion has indicator electrode and reference electrode portions adapted for electorial connection with one another, wherein the indicator and reference electrode portions are segregated from one another and the contact portion on the absorbent material. A liposome lysing agent is also bound to the absorbent material, either in the indicator electrode portion, or in a liposome lysing portion which is positioned between the contact portion and the indicator electrode portion, and which is segregated from the contact portion.

A method for detecting or quantifying an analyte using such a test device is also provided in accordance with the invention. As before, an electrolyte mixture containing the analyte, a conjugate of an analyte analog and liposomes comprising an electroactive marker, and a binding material specific for the analyte is incubated for a time sufficient to allow competition between the conjugate and the analyte for the binding material. Following incubation, the mixture is allowed to traverse the absorbent material through the electroactive measurement portion. As the electrolyte test mixture flows through the indicator electrode portion into the reference electrode portion, a potential differential is established between the two electrode portions. In addition, the liposomes are lysed by contact with the liposome lysing agent. The potential presence or amount of the difference between the two electrodes is then detected and correlated with the presence or amount of the analyte in the sample.

By "analyte" is meant the compound or composition to be measured that is capable of binding specifically to an binding material.

By "binding material" is meant a bioreceptor molecule such as an immunoglobulin or derivative or fragment thereof having an area on the surface or in a cavity which specifically binds to and is thereby defined as complementary with a particular spatial and polar organization of another molecule—in this case, the analyte. The binding material, such as an antibody, can be monoclonal or polyclonal and can be prepared by techniques that are well known in the art such as immunization of a host and collection of sera or hybrid cell line technology. The binding material may also be any naturally occurring or synthetic compound that specifically binds the analyte of interest.

IgG is a preferred binding material in accordance with the invention as it is bivalent and, therefore, tends to enhance the formation of aggregates of the conjugate and the binding material. IgM may be particularly preferred for certain applications, as its 10 binding sites per molecule would be expected to promote the formation of large aggregates.

By "receptor" is meant any compound or composition capable of recognizing a particular spatial and polar organization of a molecule, e.g., an epitope or determinant site.

Suitable receptors in accordance with the invention include those capable of binding directly with the surface of the liposomes, or with a molecule bound on adhered to the surface of the liposomes. For example, an antibody specific for a liposome tag, sufficiently different in structure from the analyte of interest can be employed as a receptor for suitably derivatized liposomes. Illustrative receptors include naturally occurring receptors, e.g., egg white avidin, streptavidin, thyroxine binding globulin, antibodies, Fab fragments, lectins, nucleic acids, protein A, protein G, and the like. For example, in the preferred embodiment of the invention, avidin or more preferably, anti-biotin antibody, function as receptors for liposomes derivatized with biotin. Alternatively, egg white aviden can be employed as the receptor, as it will bind directly to the liposome surface.

As is discussed in greater detail below, the method of the invention employs a conjugate of marker-encapsulating liposomes and an analyte analog. Certain analytes of interest may be so intractable as to make direct conjugation with the liposome inconvenient, difficult, or even impossible. In such cases, it will be necessary to employ a reactive analog of the analyte of interest to prepare the conjugate. Thus, by "analyte analog" is meant either the analyte or an analog of the analyte which will react with or bind to the liposomes. When an analog is employed, however, it is necessary that the particular characteristics of the analyte necessary for recognition by the binding material in the competition reaction be present in the analyte analog conjugated with the liposomes. The use of an analyte analog where the analyte (PCB) is intractable is illustrated in the Examples below.

By "marker accumulating agent" is meant any ion, compound, or composition capable of trapping electroactive marker materials released from the liposome interiors. Ion-exchange resins are preferred marker accumulating agents in accordance with the invention.

The mixture formed by combining the binding material, the conjugate, and the test sample may be a solution, suspension, dispersion, or other mixture.

By "absorbent material" is meant a porous material having a pore size of from 0.05 µm to 50 µm, preferably from 0.45 µm to 5 µm, which is susceptible to traversal by an aqueous medium in response to capillary force. Such materials may be natural polymeric materials, particularly cellulosic materials, such as fiber-containing papers, e.g., filter paper, chromatographic paper, etc.; synthetic or modified naturally occurring polymers, such as nitrocellulose, cellulose acetate, poly(vinyl chloride), polyacrylamide, cross linked dextran, agarose, polyacrylate, activated nylon, etc.; either used by themselves or in conjunction with a support, as described below. Nitrocellulose is a preferred absorbent material.

The absorbent material may be polyfunctional or be capable of being polyfunctionalized to permit covalent bonding of receptors as well as to permit bonding of other compounds which form a part of the signal producing system.

The absorbent material which is employed in the test device and method of the invention is generally a cellulose ester with nitrocellulose giving exceptionally good results. It is to be understood that the term "nitrocellulose" refers to nitric acid esters of cellulose, which may be nitrocellulose alone, or a mixed ester of nitric acid and other acids, and in particular, aliphatic carboxylic acids having from one to seven carbon atoms, with acetic acid being preferred. Such materials, which are formed from cellulose esterified with nitric acid alone, or a mixture of nitric acid and another acid such as acetic acid, are often referred to as nitrocellulose paper.

Although nitrocellulose is a preferred material for producing the test device, it is to be understood that other materials, having a surface area sufficient for supporting the receptor and other agents to be immobilized thereon in a concentration as hereinbelow described, and a pore size suitable for accumulating aggregates formed from the conjugate and the binding material may also be employed for producing such test devices.

In general, the absorbent material which is used in the device and method of the invention has a surface area such that is capable of supporting the receptor in an excess amount, i.e., in an amount sufficient to capture all of the conjugate which reaches the measurement zone during traversal of the absorbent material by the test mixture.

Absorbent materials having high surface areas (such as nitrocellulose) are particularly preferred in that the receptor may be supported on such materials in a high concentration.

Application of receptors, liposome lysing agents, and marker accumulating agents to the absorbent material may be accomplished by well-known techniques, for example, by spraying or spotting a solution of those materials onto the absorbent material.

The amount of receptor which is bound to the absorbent material at the measurement portion will vary depending upon the amount required to bind the unbound conjugate to enable an effective assay. Generally, the amount of receptor at the measurement portion will be at least 10 µg/cm$^2$. However, the invention is not limited to a particular concentration of receptor on the absorbent material.

The receptor and members of the signal producing system can be bound to the absorbent material by adsorption, rather than covalent bonding, as long as such binding is nondiffusive. This will involve contacting the absorbent material with a solution containing the materials to be bound to the material and allowing the material to dry. In general, this procedure will be useful only where the absorbent material is relatively hydrophobic or has a high surface charge, and subsequent treatment with proteins, detergents, polysaccharides, or other materials capable of blocking nonspecific binding sites will be required.

Before or after application of the receptor signal-producing components (i.e., the liposome lysing agent and marker accumulating agent) to the appropriate portions on the absorbent material, the residual nonspecific binding capacity of the absorbent material is saturated or blocked with one or more types of proteins or other compounds such as polyvinylpyrrolidone, polyvinylalcohol, other suitable polymeric blocking agents etc., which do not specifically bind the materials to be employed in the assay. Blocking is generally carried out after the receptor is applied to the strip, but it may be possible to block the strip before the receptor is applied depending on the particular receptor, blocking agent, and absorbent material employed. Similarly, the order of the steps of blocking the absorbent material and applying the liposome lysing agent and/or the marker accumulating agent may vary depending on the particular assay conditions and components employed. Thus, for example, the residual binding capacity of the substrate may be blocked so as to prevent nonspecific binding by the use of bovine serum albumin, as described in Towbin, et al., *Proc. Nat'l. Acad. Sci.*, 76 (1979) 4350, which is hereby incorporated by reference. The techniques for preventing non-specific binding are generally known in the art, and such techniques are also generally applicable to preventing nonspecific binding in the assay of the present invention. Examples of particularly suitable techniques for blocking with polyvinylpyrrolidone and polyvinylalcohol are described, for example, Bartles, et al. *Anal. Biochem.*, 140 (1984) 784, and in British Patent Specification GB 2204398 A, respectively, which are hereby incorporated by reference.

In conjunction with a blocking agent or agents, a surfactant may be applied to the absorbent material in a concentration sufficient to promote homogeneous flow of the test solution across the test device, to facilitate migration of the analyte analog-liposome conjugate without lysis of the liposomes. Suitable surfactants include Brij™ (polyoxyethylene ether), Tween 20™ (polyoxyethylenesorbitan monolaurate), Triton X-100™ (t-octylphenoxypolyethoxyethanol), sodium dodecylsulfate, n-octyl-β-D-glucopyranoside, Span 20™, Nonindet P-40, Chapso™, Turgitol™ and sodium dioxycholate. The concentration of the surfactant(s) employed in a blocking solution will depend, in part, upon the liposome composition. In general, surfactants may be incorporated in a concentration of from about 0 to about 0.01 volume percent of the blocking solution, preferably from about 0.001 to about 0.005 volume percent of the blocking solution. It is important that the concentration of surfactant applied to the absorbent material be controlled, as premature lysis of the liposomes may occur if the surfactant concentration is too high. Tween 20™ is a preferred surfactant for use in a blocking solution.

Figures 9A, 9B:
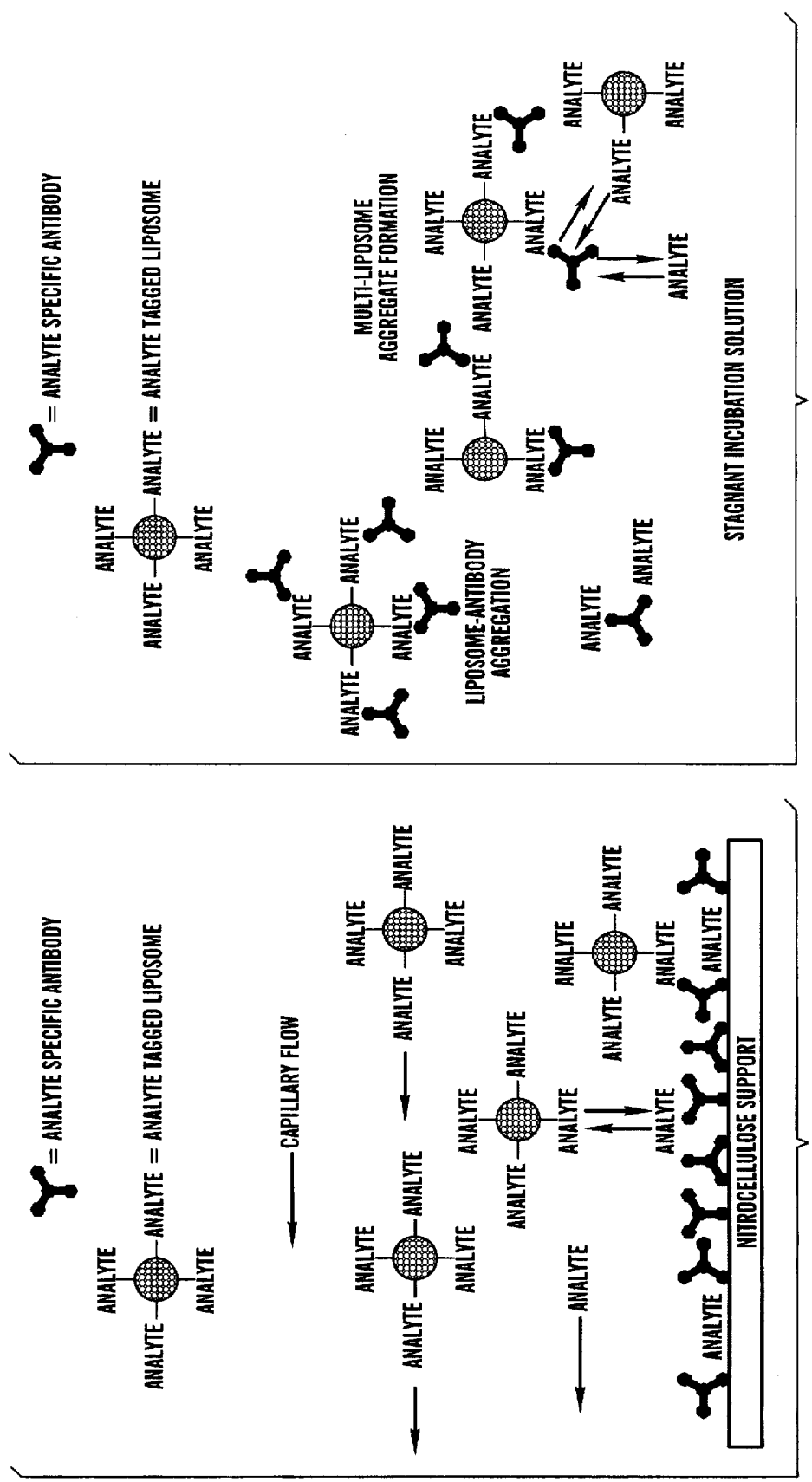
FIG. 9 is a schematic depiction of competitive binding events which occur on the test device described in copending application Ser. No. 08/135,741 (FIG. 9A) and during the incubating step in accordance with the method of the invention (FIG. 9B).

Without being bound by theory, it appears that polyvinylpyrrolidone assists in the accumulation of aggregates on the absorbent material, particularly for "Liposome-Antibody Aggregation"-type aggregates shown in FIG. 9B, described more fully below.

The blocking agents block nonspecific binding sites on the absorbent material. The blocking agents are selected from the group consisting of proteinaceous blocking reagents capable of inhibiting binding of molecules having a molecular weight of greater than about 1000 with said absorbent material and polymer blocking reagents capable of inhibiting binding of molecules having a molecular weight of less than about 1000 with said absorbent material. The proteinaceous blocking reagent may be selected from the group consisting of gelatin, non-fat dry milk, bovine serum albumin, and keyhold limpet hemocyanin. The polymer blocking reagent may be selected from the group consisting of polyvinylpyrrolidone and polyvinylalcohol, and the surfactant may be selected from the group consisting of polyoxyethylene ethers, polyoxyethylenesorbitan monolaurate, t-octylphenoxypolyethoxyethanol, and sodium dodecylsulfate, octylglucopyranoside, and sodium dioxycholate.

The absorbent material can be a single structure such as a sheet cut into strips. The absorbent material can be mounted on a support material. On the other hand, the absorbent material may provide its own support. In one embodiment of the invention, the test device is a strip of particulate material bound to a support or solid surface such as found, for example, in thin-layer chromatography. The absorbent material can be a sheet having lanes thereon, or be a uniform sheet capable of division into separate lanes by physical removal of the absorbent material from the support to induce lane formation, wherein a separate assay can be performed in each lane as shown in FIGS. 1–3 and 6–7. The absorbent material can have a shape that is rectangular, circular, oval, trigonal, or the like, provided that there is at least one direction of traversal of a test mixture by capillary migration. Other directions of traversal may occur such as in an oval or circular piece contacted in the center with the test mixture. However, the main consideration is that there be one direction of flow from the contact portion through the measurement portion. In this discussion strips of absorbent material are described by way of illustration and not limitation.

The absorbent material of the test devices in accordance with the invention preferably comprises a region for accumulation of aggregates formed from the conjugate and the binding material, as described in more detail, below. For test devices comprising electrochemical measurement portions, this region for accumulation is positioned away from the liposome lysing agent, and either between the liposome lysing agent and the contact portion, or in the contact portion. For the other test devices in accordance with the invention, this region for accumulation is positioned away from the measurement portion, and either between the measurement portion and the contact portion, or in the contact portion.

In constructing the test devices in accordance with the invention, it is desirable to position the measurement portion as close as possible to the contact portion in order to minimize the time necessary for the test mixture to reach and pass through the measurement portion. However, it is important that the measurement portion and contact portion not be so close as to contact one another, and to avoid having the test mixture come in contact with the measurement portion other than by capillary transport of the test mixture through the measurement portion. In other words, the measurement and contact portions should be separated sufficiently to avoid premature or unwanted contamination of the measurement portion through human error in manipulating the device. When there are multiple measurement portions positioned on the absorbent material (as described below for multi-analyte testing) the individual measurement zones may be close to one another and may, in certain cases, even overlap.

FIG. 1 is a schematic of a test device in accordance with the invention, depicted immediately after insertion into control mixture 209 and test mixture 208, which are held in tray 210 having partition 216 extending across the entire width of tray 210 to divide tray 210 into separate compartments for the control and test mixtures. As shown in FIG. 1, absorbent material 212 is mounted on support 214.

The test device shown in FIG. 1 is divided into two channels, namely, control channel D and test channel E, with measurement portions 206. Control channel D includes measurement portion 206d, which, as described above, has a receptor for the appropriate analyte analog-liposome conjugate bound thereto. Test channel E similarly has measurement portion 206e, which has been constructed to recognize and bind the analyte analog-liposome conjugate, respectively, as described above.

According to the embodiment of the invention shown in FIG. 1, the contact portion of each channel of the test strip is the end of the strip to be inserted into the test or control mixtures.

Test mixture 208 is typically prepared, as described below, by combining a sample known or suspected to contain the analyte with the analyte analog-liposome conjugate and a binding material specific for the analyte in an aqueous medium. In accordance with the embodiment shown in FIG. 1, control mixture 209 is typically prepared to have the same concentration of the conjugate as test mixture 208, the same concentration of binding material as test mixture 208 and a known concentration of analyte.

The mixture containing the binding material, the conjugate, and the analyte (if present) is then incubated for a time sufficient to permit the conjugate and the analyte to compete with one another for binding with the binding material. The incubation time will vary with the particular assay, however, in most cases, from about less than 1 minute to about 30 minutes will be sufficient to allow the competition reaction to reach or approach completion. Incubation times of from about 1 minute to about 30 minutes are easily achieved with the method of the invention, and are preferred, as one of the significant advantages of the present invention is the speed with which testing for analytes can be carried out. As one skilled in the art will appreciate, it is important that the competition reaction be permitted to approach completion, to avoid inaccurate results. However, it may be necessary to control the reaction time in some cases, because liposome-entrapping flocculants may form if the incubation period is too long.

Following incubation of the solution, the contact portion of absorbent material 212 of control channel D is inserted into control solution 209, while the contact portion of absorbent material 212 of test channel E is inserted into test solution 208. Wetting of absorbent material 212 by capillary action is allowed to continue at least until measurement portions 206d and 206e are wet, (and preferably, until the solvent front reaches the end of the absorbent material) with control solution 209 and test solution 208, respectively.

Control solution 209 and test solution 208 continue to traverse channels D and E of the test device into and through measurement portions 206d and 206e, where the conjugate is trapped and accumulated in measurement portions 206d and 206e by the specific conjugate receptor bound thereto. By comparing the signal intensities in measurement portions 206d and 206e, the presence of an analyte at a level considered significant as, for example, exceeding a toxicity or regulatory limit represented by a tolerance level control in portion 206d, can be determined.

As described below, qualitative measurement of the marker in measurement zones 206d and 206e may be made visually or instrumentally when the marker is a visible dye. The intensity of the color in measurement portions 206d and 206e may be visually compared with a series of reference standards, such as in a color chart, for a semi-quantitative determination of the amount of analyte in the sample. Alternatively, other types of markers, as described below, may be detected and measured using instrumentation such as a reflectometer, spectrophotometer or fluorimeter.

Figure 2:
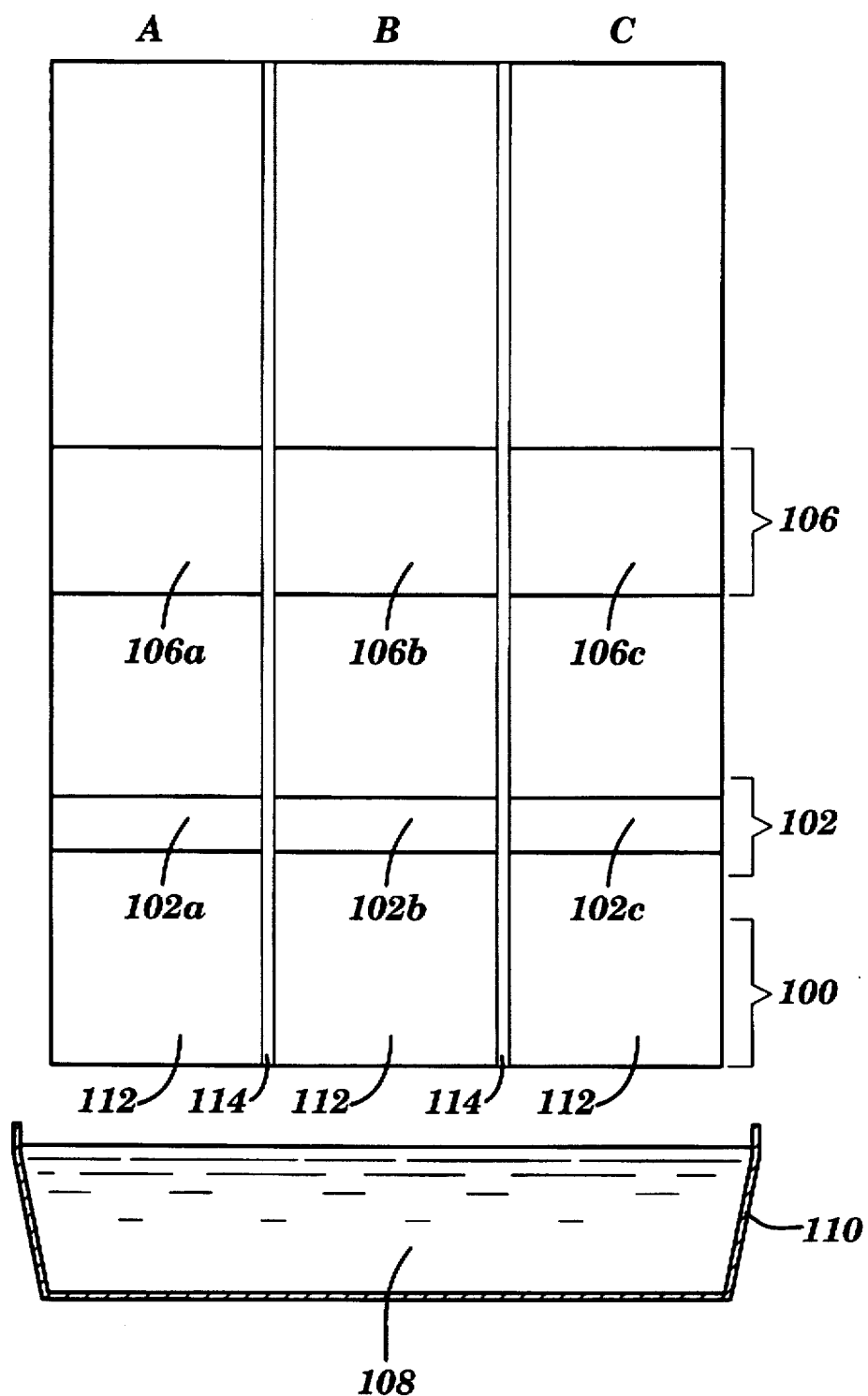
FIG. 2 is a schematic of an alternative multiple channel test device in accordance with the invention.

An alternative multiple channel test device in accordance with the invention is shown schematically in FIG. 2. In this case, the test device is shown before insertion into sample compartment 110 containing a wicking reagent such as carrier solution 108, which is generally a buffered saline solution. In the embodiment shown in FIG. 2, the test device is divided into high control channel A, test channel B, and low control channel C. As was described above in connection with FIG. 1, absorbent material 112 is supported on support 114. The test device includes wicking portions 100, contact portions 102, and measurement portions 106. High control channel A includes contact portion 102a, and measurement portion 106a. Test channel B similarly includes contact portion 102b, and measurement portion 106b. Finally, low control channel C includes contact portion 102c, and measurement portion 106c.

The test device shown schematically in FIG. 2 is designed for the simultaneous measurement of the analyte in a test sample and high- and low-level control compositions to provide linear interpolation and verification of response. A high-level control solution or mixture, the test mixture prepared and incubated as described above in connection with FIG. 1, and a low-level control solution or mixture are spotted onto contact portions 102a, 102b, and 102c, respectively, prior to insertion of the test device into carrier solution 108. Following migration of carrier solution 108 through contact portions 102a, 102b, and 102c, and measurement portions 106a, 106b, and 106c and, optionally, to the end of channels A, B and C, color intensity or other marker signal is observed or quantified in measurement zones 106a, 106b, and 106c which, as described above in connection with FIG. 1, each have the receptor for the analyte analog-liposome conjugate bound thereto.

The support for the absorbent material where a support is desired or necessary will normally be hydrophobic, water insoluble, non-porous, and rigid, and usually will be of the same length and width as the absorbent strip but may be larger or smaller. A wide variety of organic and inorganic materials, both natural and synthetic, and combinations thereof, may be employed, provided only that the support does not interfere with the production of signal from the marker. Illustrative polymers include polyethylene, polypropylene, poly(4-methylbutene), polystyrene, polymethacrylate, poly(ethylene terephthalate), nylon, poly (vinyl chloride) poly(vinyl butyrate), glass, ceramics, metals, and the like.

The size of the piece of absorbent material is dependent on several considerations. The primary consideration, as described further below, is to capture unaggregated conjugate at the measurement portion to give a sufficient signal so that a sensitive and accurate assay is achieved. The following discussion is primarily focused on strips of absorbent material for purpose of illustration and not limitation. As mentioned above, other shapes such as circular, oval, trigonal, and the like, fall equally within the scope of this invention. The dimensions thereof and other parameters can be determined by those skilled in the art with reference to the disclosure herein.

When capillary flow is predominantly upward, the length and thickness of the strip control the amount of mixture that can pass through the measurement portion. If the transfer of a large volume of test mixture is desired, the fluid capacity of the strip above the measurement portion must be sufficient to accommodate the desired volume. Alternatively, an absorbing pad or sponge may be used to contact the end of the strip opposite the end used to contact the test mixture. An absorbing pad or sponge may be used in this manner in situations when it is desirable to pull a larger volume of the test mixture across the test device so as for example, to increase the concentration of the conjugate in the measurement zone.

To permit conservation of reagents and provide for samples of limited size, the width of the strip will generally be relatively narrow, usually less than 20 mm preferably less than 10 mm. Generally, the width of the strip will not be less than about 2 mm and will usually range from about 2 mm to 10 mm, preferably from about 3 mm to 6 mm.

As is described in detail below, the test device in accordance with the invention may be modified for simultaneous multiple analyte detection or determination. The length of the strip will depend on the concentration of the analyte and practical considerations such as ease of handling and the number of measurement portions on the strip and will be about 4 cm to 20 cm, usually about 5 cm to 15 cm, preferably about 6 to 13 cm but may be of any practical length. The structure of the strip can be varied widely and includes fine, medium fine, medium, medium coarse and coarse. In general, smaller pore size and finer material will provide slow capillary flow and more efficient capture of unaggregated conjugate on the strip.

More significantly, an absorbent material having a smaller pore size will trap smaller aggregates. Courser, more porous materials provide faster flow, but the efficiency of capture is reduced. Selection of the porosity of the material depends on the rate of binding of the components for a given assay.

The position of the measurement portion (or portions, where a plurality of analytes are being determined), should be governed by the basic principle involved in the present invention. One desires to pass by capillarity a sufficient amount of the test mixture across the strip to the measurement portion to drive unaggregated conjugate through the portion of the absorbent material where conjugate aggregates are accumulating and on to bind the unaggregated conjugate at the measurement portion to produce a signal that is detectable. It is desirable to position the measurement portion close to the contact portion. Desirably, the measurement portion should be at least 3 mm, preferably at least 8 mm, from the contact portion of the strip. The measurement portion should be positioned on the absorbent material so as to enable the test mixture to pass through the measurement portion by capillary action so as to capture the unaggregated conjugate. Where several measurement portions are used for multi-analyte determinations, the measurement portions can be grouped close together or apart. Depending upon the signal production and detection system employed, it may be necessary in some cases to separate the portions so as to avoid compromising the resolution of the signals.

In carrying out the method of the invention, the protocol will normally involve combining the sample suspected of containing the analyte with the binding material and conjugate in an aqueous medium to form an aqueous test mixture or solution. The sample may be derived from a wide variety of sources, such as physiologic fluids, illustrated by saliva, sweat, serum, plasma, urine, tear fluid, spinal fluid, etc., chemical processing streams, food, waste water, natural waters, soil extracts, etc. Various addenda may be added to adjust the properties of the test mixture, or of a carrier solution used as a wicking reagent, depending upon the properties of the other components of the device, as well as on those of the liposomes or the analyte analog-liposome conjugate, or the analyte itself. Examples of solution addenda which may be incorporated into test, control, or carrier solutions or mixtures in accordance with the invention include buffers, for example, pH and ionic strength, and sample or analyte solubilizing agents, such as, for example, nonpolar solvents.

The order of addition of the test sample (suspected of containing the analyte), the binding material, and the conjugate to one another is not critical. Generally, however, it is preferred to allow the binding material and test sample to interact briefly before the addition of the conjugate to compensate for the competitive advantage enjoyed by the conjugate with its multiple binding material binding sites.

The contact portion of the absorbent material, which usually includes the end of the absorbent material to which the contact portion is proximate, is contacted with test mixture, usually by immersion of the contact portion into the test mixture. Wetting of the absorbent material by capillary action is allowed to continue at least until the measurement portion is wet, preferably until the solvent front reaches the end of the absorbent material opposite the first end.

Alternatively, the test mixture may be contacted with the absorbent material by spotting the test mixture (following incubation to form aggregates) onto the absorbent material in the contact portion. In this case, the contact portion includes a wicking portion at the first end of the absorbent material. In use, the wicking portion of the contact portion is inserted into a wicking reagent after the test mixture is spotted onto the contact portion, outside of the wicking portion.

For the most part, relatively short times are involved for the test mixture to traverse the strip. Usually, traversal of the test mixture over the strip will take at least 30 seconds and not more than ½ hour, more usually from about 1 minute to 10 minutes. In accordance with the method of the invention, the signal is rapidly, even immediately, detectable.

The conjugate of the analyte analog and the marker-encapsulating liposome may be prepared by procedures generally known in the art, with the particular procedure used in a given case being dependent upon the analyte or analog which is employed. Such techniques include covalent coupling, derivatization or activation, and the like. The liposomes may be produced from a component which has been derivatized with the analyte, whereby the liposomes, when produced, are conjugated with the analyte. In another procedure, the liposomes, including the marker, may be initially formed, followed by conjugating the liposomes with the analyte or analyte analog by procedures known in the art.

Liposomes can be prepared from a wide variety of lipids, including phospholipids, glycolipids, steroids, relatively long chain alkyl esters; e.g., alkyl phosphates, fatty acid esters; e.g. lecithin, fatty amines, and the like. A mixture of fatty materials may be employed, such as a combination of neutral steroid, a charge amphiphile and a phospholipid. Illustrative examples of phospholipids include lecithin, sphingomyelin, and dipalmitoylphosphatidylcholine, etc. Representative steroids include cholesterol, chlorestanol, lanosterol, and the like. Representative charge amphiphilic compounds generally contain from 12 to 30 carbon atoms. Mono- or dialkyl phosphate esters, or alkylamines; e.g. dicetyl phosphate, stearyl amine, hexadecyl amine, dilaurylphosphate, and the like are representative.

The liposome sacs are prepared in aqueous solution containing the marker whereby the sacs will include the marker in their interiors. The liposome sacs may be prepared by vigorous agitation in the solution, followed by removal of the unencapsulated marker. Further details with respect to the preparation of liposomes are set forth in U.S. Pat. No. 4,342,826 and PCT International Publication No. WO 80/01515, both of which are incorporated by reference.

As hereinabove indicated, the signal producing system includes a marker included in the interior of the conjugated liposomes. Suitable markers include fluorescent dyes, visible dyes, bio- and chemiluminescent materials, enzymatic substrates, and radioactive materials. Visible dyes and radioactive materials can be measured without lysis of the liposomes. However, even when liposome lysis is required, as when the other marker materials are used, a separate lysing step is not necessary, because a liposome lysing agent may be non-diffusively bound directly to the absorbent material as, for example, in the measurement zone. Suitable liposome lysing materials include surfactants such as octylglucopyranoside, sodium dioxycholate, sodium dodecylsulfate, polyoxyethylenesorbitan monolaurate sold by Sigma under the trademark Tween-20, and a non-ionic surfactant sold by Sigma under the trademark Triton X-100, which is t-octylphenoxypolyethoxyethanol. Octylglucopyranoside is a preferred lysing agent for many assays, because it lyses liposomes rapidly and does not appear to interfere with signal measurement. Alternatively, complement lysis of liposomes may be employed.

A qualitative or semi-quantitative measurement of the presence or amount of an analyte of interest may be made with the unaided eye when visible dyes are used as the marker. Alternatively, when greater precision is desired, or when the marker used necessitates instrumental analysis, the intensity of the marker may be measured directly on the absorbent material using a quantitative instrument such as a reflectometer, fluorimeter, spectrophotometer, electroanalyzer etc.

In one embodiment of the invention, a marker which is visible under the assay conditions is used so that the presence and/or amount of analyte may be determined without further treatment and without the use of instrumentation, e.g., by use of a liposome containing a dye as the marker.

In the method of the invention, a conjugate of an analyte analog and marker-loaded liposome are combined in an aqueous medium with a sample suspected of containing the analyte and a binding material specific for the analyte, to provide an aqueous test mixture. The liposomes incorporated in the conjugate have multiple analyte analog molecules bound hereto and, therefore, multiple binding sites for the binding material. In the absence of the analyte, binding material will react exclusively with the conjugate, resulting in the formation of relatively large aggregates, each of which may include multiple liposomes (see, for example, the two examples of conjugate-binding material aggregates in FIG. 9B). During migration of the test mixture across the test device, the large aggregates formed during the incubation will tend to be retained in the interstices of the nitrocellulose matrix and will form an "aggregation zone" on the absorbent material, usually at or near the meniscus of the test mixture when the device is inserted as shown in FIG. 1 into the test mixture. By occupying binding sites on the binding material, the analyte inhibits conjugate aggregation. Thus, the greater the concentration of analyte in the test sample, fewer aggregates will form and those that do form will be relatively limited in size. Smaller particles, including unaggregated liposome-analyte analog conjugate, will not be retained at the "aggregation zone" and will continue to migrate until bound in the measurement zone. The conjugates that do not aggregate will be proportional to the amount of analyte in the mixture, and will bind to the measurement portion.

A receptor capable of binding to the conjugate is preferably non-diffusively bound to the absorbent material at the measurement portion. The contact portion of the absorbent material is contacted with the test mixture, which will traverse the absorbent material through capillary action. This transversal can be upward, downward, horizontal or combinations thereof. The amount of the conjugate that becomes bound to the measurement portion through binding to the receptor is related to the amount of analyte in the sample. The signal-producing system provides a detectable signal at the measurement portion only when the conjugate is bound to the receptor in the measurement portion, so that the presence of the analyte may be determined by detecting the signal at the measurement portion. Binding of the conjugate to the receptor may occur directly to a binding site on the liposome.

The present invention provides for an immunoseparation of aggregated conjugate from unaggregated conjugate. This is accomplished as a result of the inability of aggregated conjugate to proceed beyond a certain position on the absorbent material.

The movement of the test mixture along the absorbent material is due to capillary action. This capillary movement along the absorbent material causes the test mixture to be carried to and through the measurement portion.

Measurement of the marker-loaded liposomes takes place in the measurement portion of the absorbent material. As described above, concentration or accumulation of the conjugate may be achieved by various immunospecific binding reactions as described above.

In one embodiment of the invention, the conjugate of the analyte analog and the liposomes is further conjugated to biotin. The assay is carried out in the same way but receptor for biotin is used, such as avidin or antibody specific for biotin. When analyte is present, some biotinylated conjugate reaches the measurement portion and is bound by the antibiotin or avidin. However, it has been found that egg white avidin, with the carbohydrate moiety still attached, strongly binds all of the liposomes, without the need of conjugating biotin to them. As the specificity of the assay lies in the immunorecognition reaction in the antibody zone, an avidin collection zone provides a simple solution to give the desired direct readout measurement.

In the electrochemical detection method of the invention, an electroactive species, such as ferrocyanide, is encapsulated into the liposomes. Electrodes are printed onto the strip, or the strip is placed in contact with reusable electrodes. After lysis of the liposomes, the quantity of the electroactive species is determined amperometrically or potentiometrically.

Figure 3:
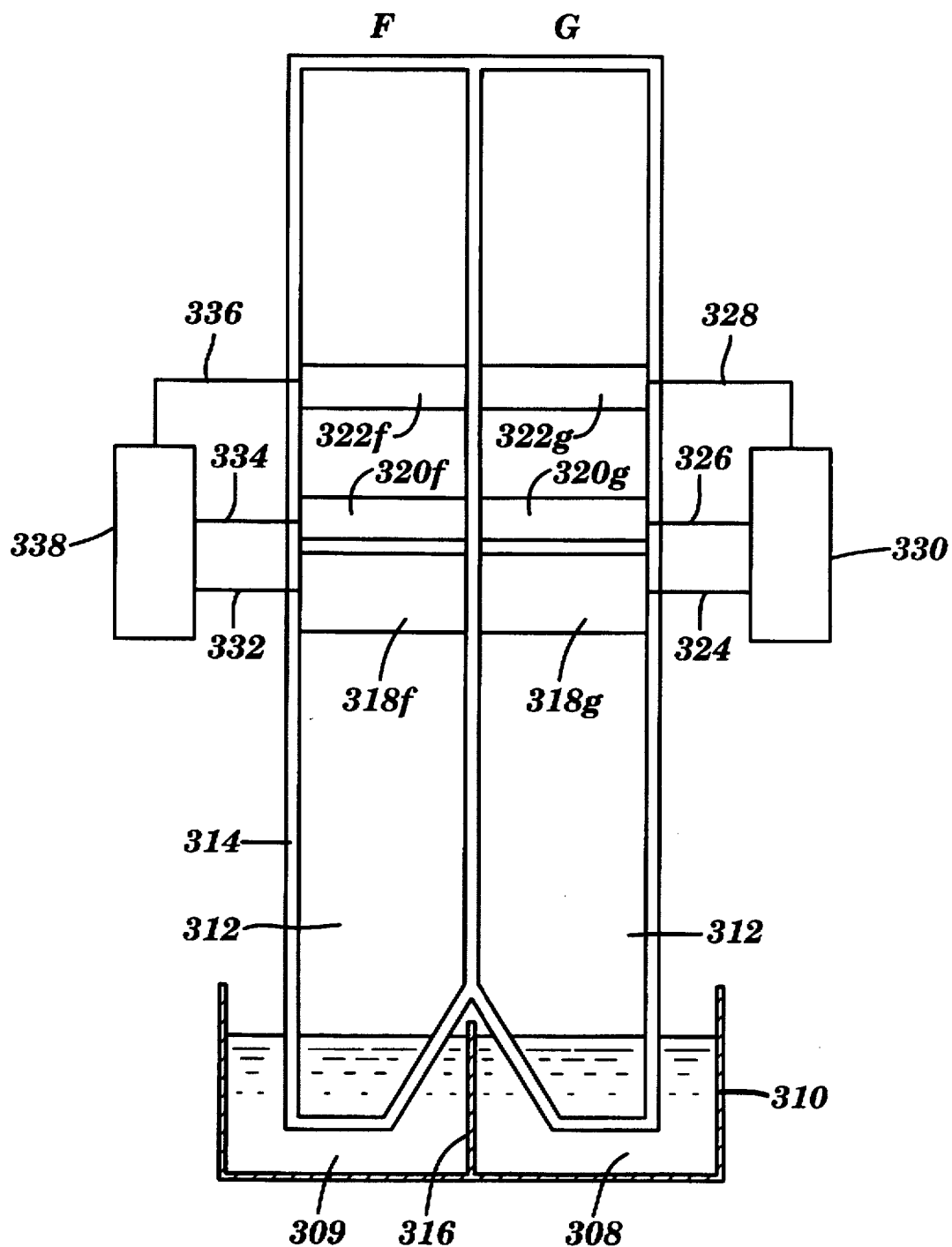
FIG. 3 is a schematic of the test device of FIG. 1, modified for electrochemical detection or determination of an analyte.

FIG. 3 is a schematic of a test device in accordance with the invention which employs electrochemical detection or measurement of an electroactive marker. The device in FIG. 3 is shown immediately after insertion into control mixture 309 and test mixture 308, which are kept separated from one another by partition 316 in tray 310. As was described above in connection with FIG. 1, the device is divided into control channel F and test channel G and includes absorbent material 312 mounted on support 314. The test device shown in FIG. 3 further includes working electrode portions 318f and 318g for control channel F and test channel G, respectively. Reference electrode portions 320f and 320g and counter electrode portions 322f and 322g are also included on absorbent material 312 of the test device, as shown in FIG. 3.

Other than the working, reference, and counter electrode portions in the embodiment shown in FIG. 3, the test device is constructed as described above in connection with FIGS. 1 and 2. Each of the electrode portions is separated from the others on the absorbent material. Working electrode portion 318f, reference electrode portion 320f, and counter electrode portion 322f are each adapted for electrical connection to one another via connections 332, 334, and 336, respectively, to potentiostat 338. Working electrode portion 318g, reference electrode portion 320g, and counter electrode portion 322g are similarly each adapted for electrical connection to one another via connections 324, 326, and 328, respectively, to potentiostat 330. In operation, the working, reference, and counter electrode portions 318g, 320g, and 322g of channel G are in electrical contact with one another, as is the case with reference electrode and working electrode portions 318f, 320f, and 322f on channel F.

Reference electrodes 320f and 320g will usually be silver or silver-silver chloride electrodes, while working electrode portions 318f and 318g, and counter electrode portions 322f and 322g may be prepared from any suitable materials such as the noble metals, other metals such copper and zinc, or carbon electrode materials in various forms, including graphitic, glassy and reticulated carbon materials. Counter electrodes 322f and 322g may be composed of the same or a different material from working electrodes 318f or 318g.

Each of the electrode portions shown in FIG. 3 may be prepared by screen printing of the electrode materials onto absorbent material 312. As is well known, screen printing involves preparation of an organic or aqueous slurry of the electrode material, typically, a fine powder of carbon, gold, etc., followed by application of the slurry across and through a silk screen onto the absorbent material of the test device. This slurry may optionally include a polymeric binder which aids in aggregating the fine metallic particles together on the surface of the absorbent material. The electrode material slurry may be fixed on the surface of the absorbent material by heating, however, the printed electrode portions are preferably allowed to air dry on the surface of the absorbent material.

The test device shown in FIG. 3 is designed for amperometric detection or quantification of an electroactive marker included in the interior of the liposomes included in the analyte analog-liposome conjugate incorporated in control solution 309 and test solution 308. Following preparation and incubation of the test solution as described above, and insertion of the test device into control mixture 309 and test mixture 308, as shown in FIG. 3, and as described above in connection with FIG. 1, the control and test mixtures are allowed to traverse the device, from the contact portions of both channels, through counter electrode portions 322f and 322g.

In the embodiment of the invention shown in FIG. 3, working electrode portions 318f and 318g may include a marker accumulating agent, such as anion-exchange polymer, non-diffusively bound thereto. Working electrode portions 318f and 318g further incorporate a liposome lysing agent, as defined above, in an amount sufficient to lyse all of the liposomes contacting the lysing agent. Alternatively, the liposome lysing agent may be bound, preferably non-diffusively, to absorbent material 312 in liposome lysing portions (not shown) located on absorbent material 312 in each of channels F and G between the contact portion (at or near the end of the device shown inserted in mixture 309) and working electrode portion 318f in channel F, and between the contact portion and working electrode portion 318g on channel G. The liposome lysing portions must be separate from the contact portions on absorbent material 312.

As control mixture 309 and test mixture 308, which are electrolyte mixtures such as saline solutions of the analyte, the binding material, and analyte analog-liposome conjugate, traverse channels F and G of the test device through working electrode portions 318f and 318g, the liposomes in the conjugate are lysed immediately before contact with or upon entry into working electrode portions 318f and 318g to release an electroactive marker substance included in their interiors. Electroactive markers are materials capable of undergoing oxidation or reduction. Suitable electroactive markers include metal ions, and organic compounds such as ascorbate, ascorbic acid, quinones, phenols, NADH. Ferrocyanide is the most preferred electroactive marker in accordance with the invention.

The electroactive marker released from the interior of the liposomes incorporated in the analyte analog-liposome conjugates in control mixture 309 and test mixture 308 are then accumulated by the ion-exchange material bound to working electrode portions 318f and 318g throughout the period during which the control and test electrolyte mixtures migrate past reference electrode portions 320f and 320g to counter electrode portions 322f and 322g. At that point, the electrical circuits between the working, reference, and counter electrode portions of each of channels F and G is automatically completed and electrolysis of the accumulated electroactive marker occurs. The current flowing through the circuits, which is directly proportional to the amount of marker released by the liposomes, and corresponds to the amount of analyte in the sample, is then measured by potentiostat 330. Devices which may be used as potentiostats in accordance with the invention include the Cypress System Electrochemical Analyzer and the BAS Electrochemical Analyzer.

Figure 6:
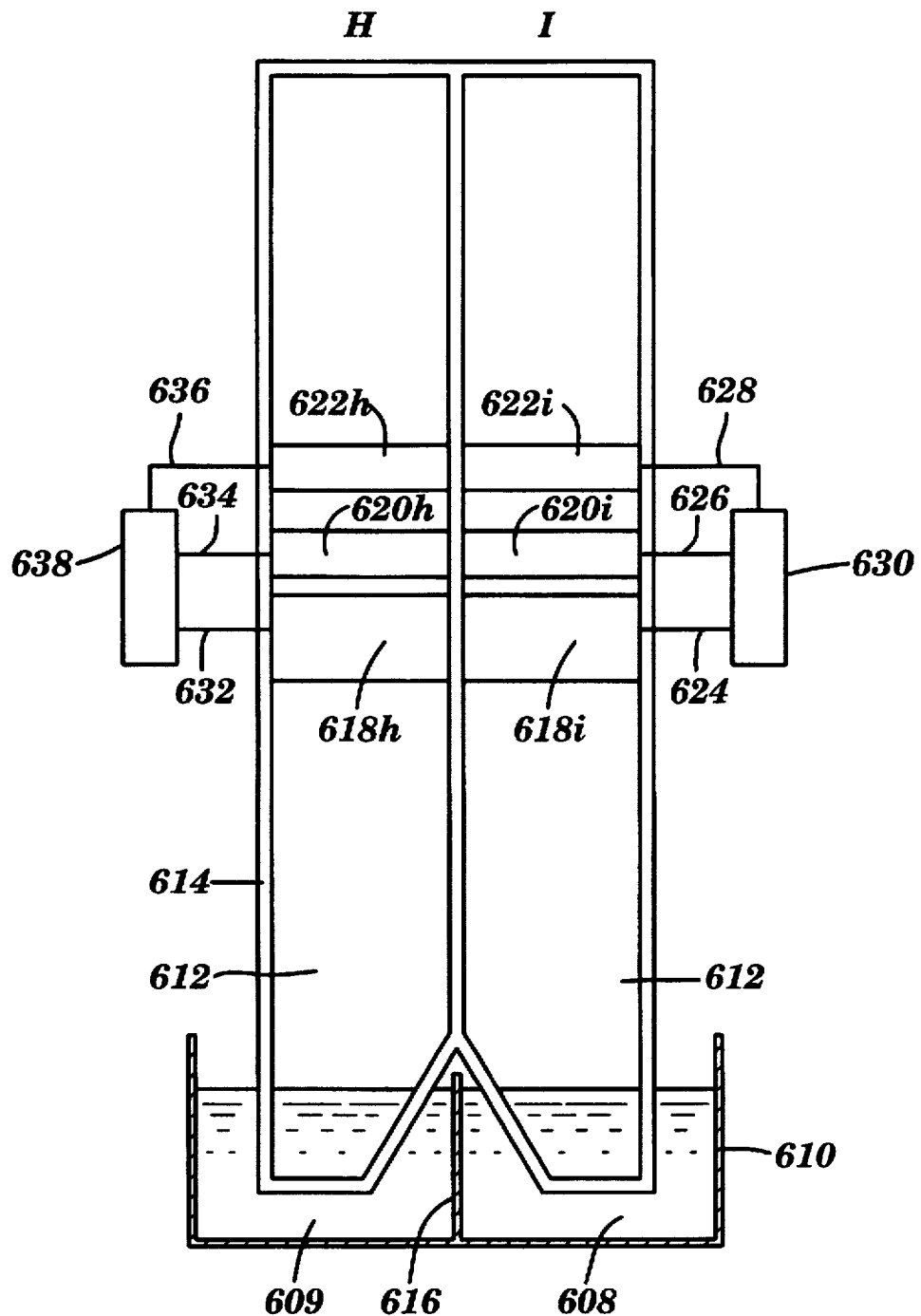
FIG. 6 is a schematic of an alternatively modified electrochemical test device.

An alternative design for a test device constructed for electrochemical detection or quantification of a liposome-encapsulated electroactive marker is shown schematically in FIG. 6. Electrolyte control solution 609 and electrolyte test solution 608, separated by a partition 616 in tray 610, are as described above in connection with the corresponding features shown in FIG. 3. Similarly, the test device shown in FIG. 6, comprising control channel H and test channel I, each of which comprises absorbent material 612 mounted on support 614, are as described above for the corresponding structures described above in connection with FIG. 3. The device shown in FIG. 6 further includes working electrode portions 618$h$ and 618$i$, reference electrode portions 620$h$ and 620$i$, and counter electrode portions 622$h$ and 622$i$, which are separated from one another on absorbent material 612. Working electrode portion 618$h$ is adapted for electrical connection to potentiostat 638, and through potentiostat 638 to reference electrode portion 620$h$ and counter electrode portion 622$h$, via connection 632. Working electrode portion 618$i$ is similarly adapted for electrical connection to potentiostat 630, and through potentiostat 630 to reference electrode portion 620$i$ and counter electrode portion 622$i$, via connection 624.

Similarly, reference electrode portions 620$h$ and 620$i$, and counter electrode portions 622$h$ and 622$i$, are adapted for electrical connection through connections 634 and 626, and through connections 636 and 628, respectively, to potentiostats 638 and 630.

The test device shown in FIG. 6 further incorporates a liposome lysing agent preferably, bound to a absorbent material 612, either in working electrode portions 618$h$ and 618$i$, or, alternatively, in separate liposome lysing portions (not shown) on absorbent material 612 in each of channels H and I between the contact portion 604$h$ and working electrode portion, on control channel H, and between the contact portion and working electrode portion 618$i$ on absorbent material 612 of test channel I. As in the case of the device shown in FIG. 3, the separate liposome lysing portions must be separated from the contact portions on absorbent material 612 in each of channels H and I. However, it is not necessary that the liposome lysing portion be separated from working electrode portions 618$h$ and 618$i$.

In contrast to the device shown in FIG. 3, the device shown in FIG. 6 does not include a marker accumulating agent in working electrode portions 618$h$ and 618$i$. In operation, traversal of the test device by electrolyte control solution 609 and electrolyte test solution 610 proceeds as described previously in connection with FIG. 3 through working electrode portions 618$h$ and 618$i$, reference electrode portions 620$h$ and 620$i$, and counter electrode portions 622$h$ and 622$i$, however, electroactive marker released as a result of contact between the analyte-liposome conjugate and the liposome lysing agent incorporated on absorbent material 612 in each of control channel H and test channel I is not accumulated in working electrode portions 618$h$ and 618$i$. In this embodiment of the invention, once the electrical circuits between counter electrode portions 622$h$ and 622$i$, and working electrodes 618$h$ and 618$i$ are completed, electrolysis of the released electroactive marker occurs continuously as the marker flows past working electrode portions 618$h$ and 618$i$. The current measured by potentiostats 630 and 638 is then integrated for a fixed period of time to provide a measure of the amount of analyte in test solution 608.

Figure 7:
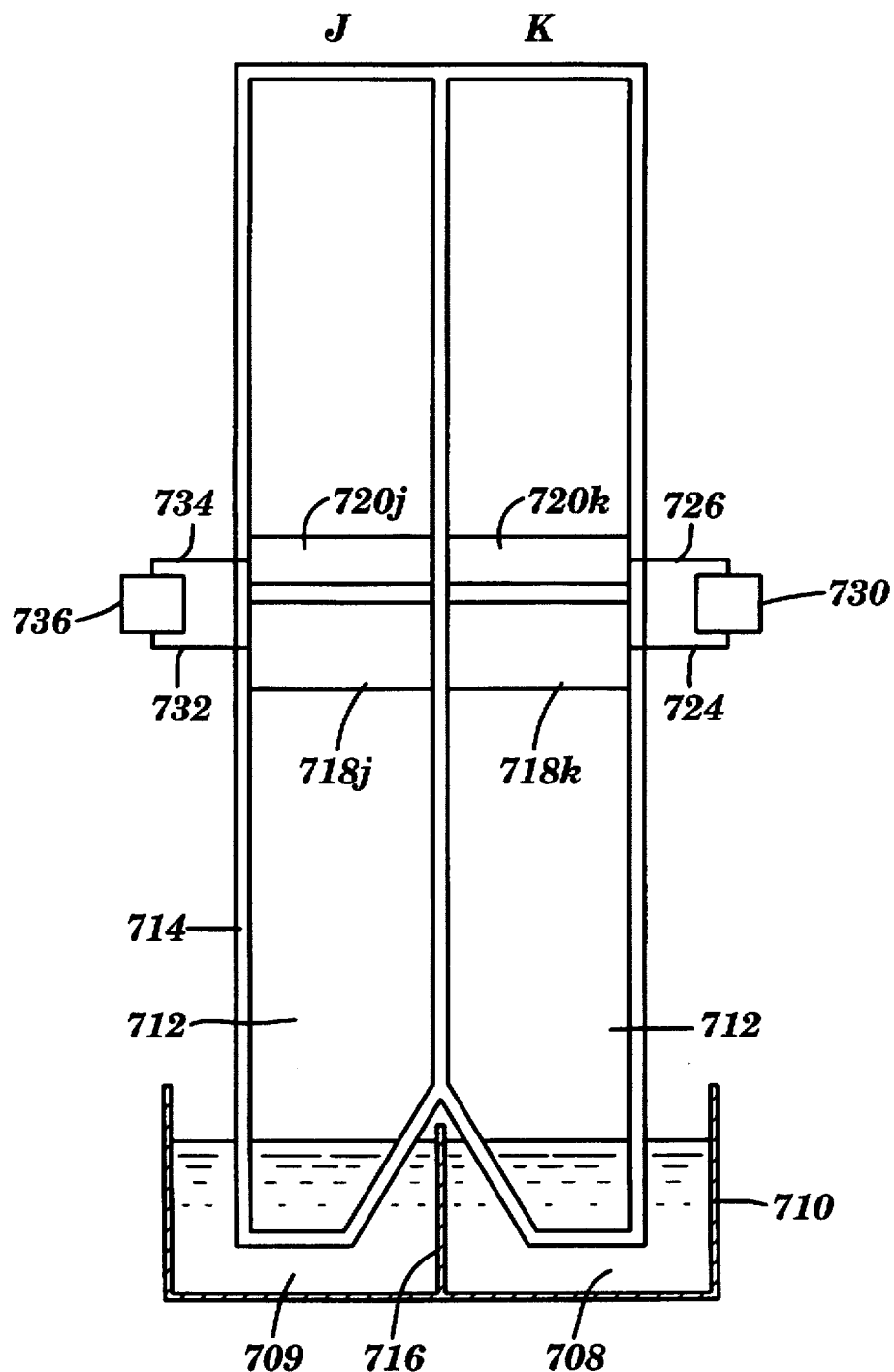
FIG. 7 is a schematic of yet another test device suitable for electrochemical detection or determination of an analyte.

Yet another embodiment of the test device of the present invention employ electrochemical detection is shown schematically in FIG. 7. In this case however, the potentiometric measurement of an electroactive marker released from the interior of the liposomes comprising the analyte analog-liposome conjugate is made. As was the case with the device shown in FIG. 6, electrolyte control solution 709 and electrolyte test solution 708 are kept separated by partition 716 in tray 710. The test device shown in FIG. 7 is constructed as was described above in connection with FIGS. 3 and 6, and includes control channel J and test channel K, each comprising absorbent material 712 mounted on support 714. As was the case with FIGS. 1, 3, and 6 described above, the device in FIG. 7 is shown immediately after insertion of the contact portion of each of channels J and K into control solution 709 and test solution 708, respectively.

In the case of the test device shown FIG. 7, the device comprises indicator electrode portions 718$j$ and 718$k$, and reference electrode portions 720$j$ and 720$k$, which electrode portions are separated from one another on absorbent material 712, as shown in FIG. 7. Indicator electrode portions 718$j$ and 718$k$, and reference electrode portions 720$j$ and 720$k$ are adapted for electrical connection to potentiometers 736 and 730 through connections 732 and 724, respectively, for indicator electrode portions 718$j$ and 718$k$, and 734 and 726, respectively, for reference electrode ortions 720$j$ and 720$k$.

As was described above in connection with FIG. 3, reference electrode portions 720$j$ and 720$k$ may be prepared, as described above, by screen printing a slurry of finely divided silver powder onto absorbent material 712. Indicator electrode portions 718$j$ and 718$k$ may be prepared in the same way from any suitable ion-selective electrode materials such as, for example, silver sulfide, or by application of ion-selective ionophores in a polymeric matrix, as described in Freiser, H. *Ion-Selective Electrodes in Analytical Chemistry*, hereby incorporated by reference.

It is necessary to incorporate a liposome lysing agent on absorbent material 712 of the test device shown in FIG. 7 between the contact portion and reference electrode portion 720$j$ of channel J and between the contact portion and reference electrode portion 720$k$ of channel K. However, as was described above in connection with FIGS. 3 and 6, the liposome lysing agent may either be bound to absorbent material 712 in indicator electrode portions 718$j$ and 718$k$, or may it be bound to a separate liposome lysing portion located on absorbent material 712 between the contact portion 704$j$ and indicator electrode portion 718$j$ in channel J, and between the contact portion 704$k$ and indicator electrode portion 718$k$ in channel K. As before, it is necessary that such liposome lysing portions be separated from the contact portions on absorbing material 712 in channels J and K.

Traversal of channel J by electrolyte control solution 709 and simultaneous traversal of channel K by electrolyte test solution 708, from the contact portions of channels J and K, proceeds as described above in connection with FIGS. 3 and 6. As control solution 709 and test solution 708 migrate through indicator electrode portions 718j and 718k into reference electrode portions 720j and 720k, a potential differential is set up between the indicator and reference electrode portions in each channel. These potential differentials are measured by potentiometers 736 and 730, which may be pH/mV meters, such as those available from Orion, Corning, or Beckman. The potential differentials are directly proportional to the concentrations of the electroactive markers released from the liposome interiors, and correspond to the concentrations of the analyte in the control and test solutions.

It should be noted that although the working, counter, and reference electrode portions in FIGS. 3 and 6, and the reference and indicator electrodes in FIG. 7 have been shown in specific positions, the positions can be otherwise than shown. Specifically, for example, the relative positions of the reference and working electrode portions in FIGS. 3 and 6 may be reversed. Similarly, the positions of the reference and indicator electrodes shown in FIG. 7 may be reversed. Although the counter electrode portions in FIGS. 3 and 6 will usually be as shown with respect to the working and reference electrode portions, even the position of the counter electrode within the electrochemical measurement portion is not critical. It is important to recognize that no immobilized receptor is required with the test devices adapted for electrochemical measurement in accordance with the invention.

The solvent for the test solution will normally be an aqueous medium, which may be up to about 40 weight percent of other polar solvents, particularly solvents having from 1 to 6, more usually of from 1 to 4, carbon atoms, including alcohols, dimethylformamide and dimethylsulfoxide, dioxane and the like. Usually, the cosolvents will be present in less than about 20 weight percent. Under some circumstances, depending on the nature of the sample, some or all of the aqueous medium could be provided by the sample itself.

The pH for the medium will usually be in the range of 4–10, usually 5–9, and preferably in the range of about 6–8. The pH is chosen to maintain a significant level of binding affinity of the binding members and optimal generation of signal by the signal producing system. Various buffers may be used to achieve the desired pH and maintain the pH during the assay. Illustrative buffers include borate, phosphate, carbonate, tris, barbital and the like. The particular buffer employed is usually not critical, but in individual assays, one buffer may be preferred over another.

The concentration of electrolytes in the medium will usually be adjusted to achieve isotonicity or equi-osmolality with the solution in the interior of the liposomes to prevent their crenation or swelling.

Electrochemical measurement in accordance with the invention may also be carried out using stripping voltametry.

Moderate, and desirably substantially constant, temperatures are normally employed for carrying out the assay. The temperatures for the assay and production of a detectable signal will generally be in the range of about 4°–45° C., more usually in the range of about 10°–38° C., and frequently, will be ambient temperatures, that is, about 15°–25° C.

The concentration, in the liquid sample, of analyte which may be assayed will generally vary about $10^{-3}$ to about $10^{-15}$M, more usually from about $10^{-5}$ to $10^{-10}$M. Considerations such as the concentration of the analyte of interest and the protocol will normally determine the concentration of the other reagents.

With the test device and method of the invention, one may also assay a test solution for a plurality of analytes such as toxic chemicals, or screen for one or more of a plurality of analytes. In one embodiment, the test device includes multiple measurement portions, each of which has a distinctive receptor specific for one of several conjugatable ligands, which are chosen, in part, so as not to interfere with any of the analytes of interest. The test solution, and control solution, where appropriate, are formed by mixing together in an aqueous medium the sample and a plurality of liposome conjugates each of which comprises (a) an analog for one of the analytes and (b) a ligand which will bind specifically to one of the receptors in one of the measurement portions of the device. Thus, the strip contains a separate measurement portion for each analyte. A mixture of binding materials specific for each of the analytes is then employed in the test solution. The conjugate of each of the analytes to be determined in this embodiment of the invention, may include a marker which is detectable distinctly from the other markers. With different encapsulated dyes, the results of the assay can be "color coded". Alternatively, each analyte may be determined by assignment of each conjugate/analyte to its own measurement portion for concentration and measurement.

In an alternative multiple-analyte embodiment, the measurement portion has bound thereto separate receptors capable of binding different analyte analog-liposome conjugates through the recognition of the receptors for separate ligands on the different analyte analog-liposome conjugates. Using such a device, it is possible to conduct a screening assay to determine, for example, whether any of a group of analytes is present in the sample. Alternatively, the liposomes attached to each analyte analog can have a different dye encapsulated, and a multi-wavelength detector can be used in a measurement portion, such as an egg-white avidin portion.

As a matter of convenience, the present device can be provided in a kit in packaged combination with predetermined amounts of reagents for use in assaying for an analyte or a plurality of analytes. Aside from the absorbent test device and the analyte analog-liposome conjugate, other additives such as ancillary reagents may be included, for example, stabilizers, buffers, and the like. The relative amounts of the various reagents may be varied widely, to provide for concentration in solution of the reagents which substantially optimizes the sensitivity of the assay. The reagents can be provided as dry powders, usually lyophilized, including excipients, which on dissolution will provide for a reagent solution having the appropriate concentrations for performing the assay. The kit or package may include other components such as standards of the analyte or analytes (analyte samples having known concentrations of the analyte).

Figure 4:
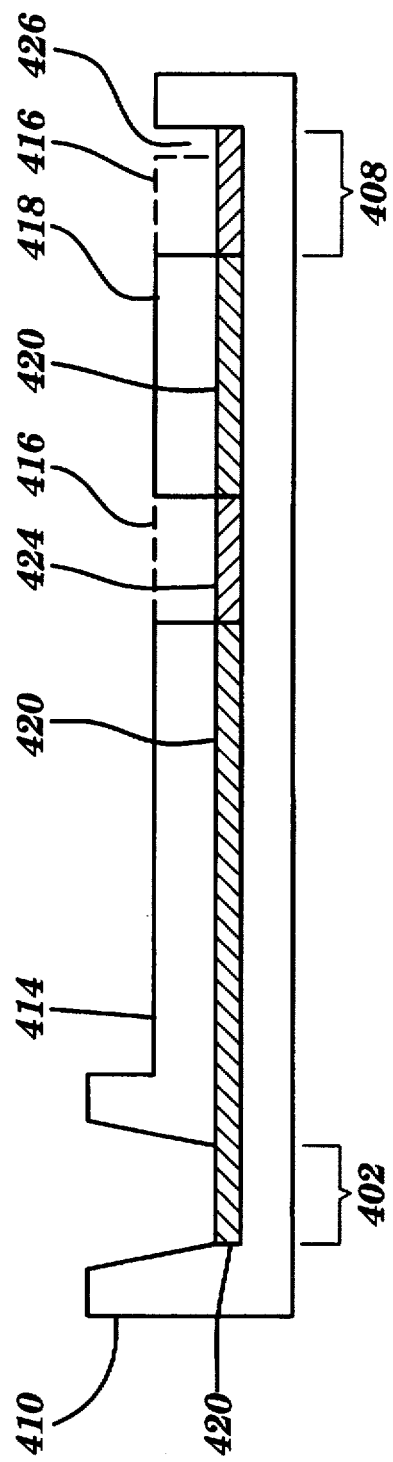
FIG. 4 is a schematic of a cross-section of a commercially useful test device in accordance with the invention.

FIG. 4 is a schematic of a cross-section of a commercially useful test device in accordance with the invention. Absorbent material 420 is supported on strip holder 410, which may be composed of any inert rigid or semi-rigid support material and is preferably composed of plastic. As described above in connection with FIGS. 1 and 2, absorbent material 420 includes contact portion 402, and measurement portion 424, having a receptor for a conjugate of an analyte analog and marker-encapsulating liposomes bound thereto. In the embodiment of the invention shown in FIG. 4, the absorbent material of the test device also includes end-point indicator portion 408, as described below. Compartment covers 414 and 418 provide further support and protection for absorbent material 420. Covers 414 and 418, which are constructed of the same or similar rigid or semi-rigid support materials as strip holder 410, may, with strip holder 410, comprise a single molded piece. Alternatively, covers 414 and 418 may be prepared from a transparent material which allows viewing of absorbent material 420, and may be connected to strip holder 410.

The device shown in FIG. 4 further include windows 416 which provide visual access to measurement portion 424 and end-point indicator portion 408 of the absorbent material. Windows 416 may be made from a transparent material such as plastic or glass. Alternatively, they may be prepared from an opaque material such as a colored plastic incorporating holes through which absorbent material 420 may be seen. Air vent 426 provides an outlet for air forced out of absorbent material 420 as a test solution or control solution migrates along absorbent material 420 from contact portion 402 to end-point indicator portion 408.

The embodiment shown in FIG. 4 provides a sturdy, portable, contamination-resistant test device suitable for use in the field. In use, a test solution containing the appropriate analyte analog-liposome conjugate, a binding material specific for the analyte, and known or suspected to contain the analyte, is incubated as described above, and then is spotted or dropped onto contact portion 402 of absorbent material 420. Contact portion 402 is wet with the test or control solution, or a carrier solution or wicking reagent after initial application of the test or control solution, until the solution traverses the absorbent material 420 from contact portion 402 to end-point indicator portion 408. Conjugate which is not aggregated and accumulated at or near the contact portion is accumulated in measurement portion 424 as a result of the binding reaction between the conjugate and the receptor bound to measurement portion 424.

The signal from the marker may be visually read through window 416 over measurement portion 424. Alternatively, the signal from accumulated liposome-encapsulated marker may be instrumentally read by, for example, a spectrophotometer which is adapted for use with the device in accordance with the invention.

In an alternative technique for incubating and introducing the test mixture or solution onto the contact portion 402 shown in FIG. 4, a layer of a material which will gradually dissolve upon contact with the test mixture may be applied to absorbent material 420 over contact portion 402. The test sample, conjugate, and binding material can then be combined and poured into the sample well of the device shown in FIG. 4, onto the dissolving layer, or the test mixture components may be introduced individually into the well. The dissolving layer thus serves as a barrier between the test mixture and contact portion 402 during incubation. During incubation, the layer gradually dissolves, and the test mixture contacts contact portion 402.

Upon penetration of the layer by the test mixture, the mixture is drawn across the absorbent material, through measurement portion 424, to end-point indicator portion 408, as described above. The dissolving layer may be formed from any suitable material which will not interfere with the assay and which will gradually dissolve upon contact with the test mixture, such as, for example, hard-caked sucrose on cellulose membrane materials.

FIG. 8 is a side-by-side schematic comparison of test devices substantially as described in copending application Ser. No. 08/135,741 (FIG. 8A) and test devices in accordance with the invention (FIG. 8B). In each of FIGS. 8A and 8B, the devices are depicted with increasing test sample concentrations of PCBs from left to right.

Specifically, the test devices shown in FIG. 8A have competitive binding portions 804 (from left to right 804c, 804d, and 804e, respectively), and measurement portions 806 (from left to right, 806c, 806d, 806e, respectively), on absorbent material 812. The devices shown in FIG. 8B have measurement portions 860 (from left to right, 860f, 860g, and 860h, respectively), on absorbent material 880. FIG. 8B illustrates test devices used in accordance with the method of the invention (i.e., the steps of combining the binding material, test sample, and conjugate to form a mixture, incubating the mixture to allow competition, and allowing the mixture to traverse the absorbent material from the contact portion through the measurement portion). Accordingly, FIG. 8B includes regions for accumulation of aggregates formed from the conjugate and the binding material ("aggregation zones") 840 (from left to right, 840f, 840g, and 840h), illustrating where accumulation of aggregates in accordance with the invention has occurred relative to the position of the measurement portion on the strip.

As is described more fully below, portions 806 in FIG. 8A and 860 in FIG. 8B are analogous in that they are each measurement or "collection" portions and have, therefore, been designated in FIG. 8 as C1 and C2, respectively. Portions 804 in FIG. 8A and 840 in FIG. 8B have been designated R1 and R2, respectively, to indicate their relationship with the competitive binding reactions which occur in the methods described in copending application Ser. No. 08/135,741 (depicted in FIG. 8A) and the present invention (depicted in FIG. 8B). With the device and method described in copending application Ser. No. 08/135,741, competitive binding occurs in competitive binding portions 804 shown in FIG. 8A, whereas, in the method of the invention, the competitive binding reaction occurs away from the strip in the mixture of the test sample, conjugate, and binding material. Thus, although the competitive binding reaction in the method of the invention it does not occur on the strip, aggregation zones 840 are the portions of the strips where accumulation of the aggregates formed during competition occurs and are, in this way, related to the competitive binding reaction.

The present invention is applicable to procedures and products for determining a wide variety of analytes. As representative examples of types of analytes, there may be mentioned: environmental and food contaminants, including pesticides and toxic industrial chemicals; drugs, including therapeutic drugs and drugs of abuse; hormones, vitamins, proteins, including antibodies of all classes; peptides; steroids; bacteria; fungi; viruses; parasites; components or products of bacteria, fungi, viruses, or parasites; allergens of all types; products or components of normal or malignant cells; etc. As particular examples, there may be mentioned $T_4$; $T_3$; digoxin; hCG; insulin; theophylline; leutinizing hormones and organisms causing or associated with various disease states, such as streptococcus pyrogenes (group A), Herpes Simplex I and II, cytomegalovirus, chlamydiae, etc. The invention may also be used to determine relative antibody affinities.

As hereinabove indicated, the assay may be qualitative (presence or absence of certain level of analyte) or quantitative or semi-quantitative. The preparation of suitable standards and/or standard curves (the term "standard curve" is used in a generic sense to include a color chart) is deemed to be within the scope of those skilled in the art from the teachings herein.

The method of the invention, and preparation and use of the test device in accordance with the invention, are illustrated by the following Examples.

EXAMPLES

Examples 1 and 2 illustrate preparation and use of a test device substantially as shown and described in co-pending application Ser. No. 08/135,741. The device and methods described in Examples 1 and 2 are hereinafter referred to as the "liposome immunocompetition" or "LIC" format for convenience.

Materials for Examples 1 and 2

Alachlor was purchased from Chem Service (West Chester, Pa.). Bovine serum albumin (BSA), N-succinimidyl-S-acetylthioacetate (SATA), dipalmitoyl phosphatidyl ethanolamine (DPPE), cholesterol, poly (vinylpyrrolidone) (PVP, 10,000 mol. wt.), Tween-20, triethylamine, Molybdenum Blue spray reagent, Isosulfan Blue and Sephadex G-50 were purchased from Sigma (St. Louis, Mo.). Dipalmitoyl phosphatidyl choline (DPPC) and dipalmitoyl phosphatidyl glycerol (DDPG) were obtained from Avanti Polar Lipids (Alabaster, Ala.). Sulforhodamine B was purchased from Eastman (Rochester, N.Y.), and Fast Green FCF from Allied Chemical (New York, N.Y.). Carnation non-fat dry milk powder (CNDM) was obtained locally. Protein assay dye reagent, goat anti-rabbit IgG alkaline phosphatase conjugate and the substrates for alkaline phosphatase were purchased from Bio-Rad (Hercules, Calif.). Egg white avidin was obtained from Molecular Probes (Eugene, Oreg.). Whatman (Maidstone, UK) silica gel TLC flexible plates and preparatory silica gel plates, both containing fluorescent indicator, were used. Plastic-backed nitrocellulose membranes with pore size >3 μm were obtained from Schleicher and Schull (Keene, N.H.). A Paasch VL airbrush (Texas Art Supply, Houston, Tex.) was used for applying the antibody and egg white avidin to the membrane. The rabbit anti-Alachlor IgG used in preliminary investigations was supplied by ImmunoSystems (Scarborough, Me.). Subsequent supplies of antiserum were provided by the Cornell University College of Veterinary Medicine.

Example 1

Preparation of Materials and Reagents

Conjugate and antibody production

Alachlor was conjugated to BSA by modification of a published method, as described in Reeves, et al. *Anal. Lett.*, 26 (1993) 1461, hereby incorporated by reference. Antibodies to the immunogenic conjugate were raised in New Zealand white rabbits by standard procedures. The antibodies produced were purified by the caprylic acid-ammonium sulfate precipitation method, described in McKinney, et al., *J. Immunol. Methods*, 96 (1987) 271, hereby incorporated by reference.

Antibody and avidin immobilization

In the strip assay, a protein-binding membrane (absorbent material) with a plastic backing to provide rigidity was required, and nitrocellulose membrane supported in this manner was found to be the most suitable. An airbrush was used to dispense the antibody and egg white avidin solutions for immobilization. The membrane was cut to a desired size (7.9 cm high and a suitable width for later subdivision into strips 5 mm wide), thoroughly wetted with 10% methanolic TES (tris buffered saline, pH 7.0) and dried before application of antibody and avidin solutions. The membrane sheet was mounted on a mobile platform that moved at a constant rate in front of the airbrush used to spray the antibody solution at a concentration between 0.2 and 1 mg ml$^{-1}$ (depending on preparation) onto the competitive binding portion of the membrane, and egg white avidin solution at 1 mg ml$^{-1}$ onto the measurement portion of the membrane. The protein bands were allowed to vacuum dry for 1 hour.

After applying antibody and egg white avidin to the nitrocellulose sheets, it was necessary to block the membrane to reduce nonspecific binding and to aid the mobility of the liposomes. Both PVP and BSA were found to be suitable for this purpose, but the former was less expensive and more tractable and was routinely used as the blocking agent. Non-uniform migration of liposomes with certain batches of membrane, can be alleviated by the use of very low levels of detergent in the blocking solution. Tween-20 at 0.002% was found suitable for this purpose, and at this level of application it did not cause lysis of the liposomes during the 8-min analysis run.

The coated nitrocellulose sheet was then immersed in blocking agent (a solution of 2% polyvinylpyrrolidone and 0.002% Tween-20 in TBS) for 1 hour on a rotating shake and dried under vacuum for 3–4 hours. Prepared sheets were stored at 4° C. in the presence of silica gel desiccant until ready for use. The sheets were cut into strips using a paper cutter when required. The final strips were 5×79 mm with a 5 mm long antibody zone 15 mm above the bottom of the strip and a similar egg white avidin zone 35 mm from the bottom.

Analyte-lipid conjugation

To provide the requisite antigenic sites (epitopes) on the surface of the liposomes for the competitive assay format, it is necessary to form a conjugate between the analyte molecule and a lipid. DPPE, which is then incorporated into the liposome bilayer.

For conjugation of the Alachlor to DPPE, a thiolating reagent, SATA, described in Duncan, et al., *Anal. Biochem.*, 132 (1983) 68, which is hereby incorporated by reference, was used as the coupling agent based on a modification of a procedure reported in Feng, et al., *J. Agric. Food Chem.* 38 (1990) 59, hereby incorporated by reference. Twenty mg of DPPE were suspended in 3 ml of 0.7% triethylamine in chloroform and sonicated under nitrogen for 1 minute in a 45° C. bath. To the DPPE, 2 molar equivalents of SATA in 1 ml of the same solvent were added slowly. The reaction flask was capped and stirred at room temperature for ca. 20 minutes, the end point of the reaction being indicated by the clearing of the mixture. The solvent was removed on a rotary vacuum evaporator, and 2 ml of 30 mM hydroxylamine hydrochloride in methanol, adjusted to pH 8.2 with NaOH, were added. The reaction mixture was vortexed vigorously and stirred at 45° C. for 1 hour under nitrogen, maintaining the pH at 8.2 using dilute NaOH in methanol. A 2.8 molar excess (to DPPE) of Alachlor in 1 ml of 30 mM hydroxylamine, pH 8.2 in methanol, was added to the reaction flask. The reaction mixture was stirred at 45° C. for 2 hours, with the pH being maintained at 8.2, and the reaction was allowed to continue at 45° C. overnight (ca. 17 hours). The product was purified on a preparatory silica gel plate using the solvent system chloroform-acetone-methanol-glacial acetic acid-water (60:20:20:5:4, v/v). The purified Alachlor-DPPE conjugate was quantified by Bartlett's phosphorous assay described in Bartlett, *J. Biol. Chem.*, 234 (1959) 466, which is hereby incorporated by reference.

Because radioactive Alachlor was not available for use as a tracer, confirmation of the successful conjugation reaction was achieved by a combined thin-layer chromatographic and an enzyme immunostaining method described in Mattsby-Baltzer, *Eur. J. Biochem.*, 138 (1984) 333, hereby incorporated by reference, using an anti-Alachlor antibody supplied by ImmunoSystems. The procedure involved the duplicate chromatographic analysis of the reaction mixture on TLC plates. Whatman Silica Gel/UV plates were prewashed in the solvent described above and dried, and the samples were run in the same solvent. One of the TLC plates was dried, blocked for 1 hour in a solution of 1% BSA and 0.5% CNDM in TBS, washed three times for 10 minutes each in TBST (TBS containing 0.05% Tween-20), and placed overnight in a solution containing the antibody to Alachlor (20 μg/ml in TBST). The plate was washed three times for 10 min each in TBST and placed in a solution containing a goat anti-rabbit alkaline phosphatase conjugate (stock diluted 1:3000 with TBST containing 0.02% BSA) for 2 hours. The plate was washed as before and developed with the substrate for alkaline phosphatase (nitroblue tetrazolium in aqueous DMF with magnesium chloride and 5-bromo-4-chloro-3-indolyl phosphate in DMF, prepared according to the manufacturer's instructions). When color development was complete (10 min), the plate was washed in distilled water and dried. A purple spot indicated the presence of Alachlor. The other TLC plate was sprayed with molybdenum blue reagent (1.3% molybdenum oxide in 4.2M sulfuric acid) which is specific for phospholipids. The Alachlor-DPPE spot appeared purple with the alkaline phosphatase substrate stain and blue with the molybdenum blue spray reagent.

Preparation of dye-encapsulated Alachlor-tagged liposomes

Liposomes were formed by the reversed-phase evaporation method, as described in Szoka, et al., *Biochim. Biophys. Acta*, 601 (1980) 559, and O'Connell, et al., *Anal. Chem.*, 31 (1985) 142, the disclosures of which are hereby incorporated by reference, from a mixture of DPPC, cholesterol, DPPG, and Alachlor-DPPE conjugate in a molar ration of 5:5:0.5:0.01. Forty-three μmol of this mixture were dissolved in 4.2 ml of a solvent mixture containing chloroform-isopropyl ether-methanol (6:6:1, v/v). This solution was warmed to 45° C. and 0.7 ml of the dye solution was added with swirling. This mixture was sonicated for 5 minutes under a low flow of nitrogen. The organic phase was removed under vacuum on a rotary evaporator at 40° until all frothing had stopped. An additional 1.3 ml aliquot of the dye solution was added, and the liposomes were then sequentially extruded twice through each of two polycarbonate filters of decreasing pore sizes of 1.0 μm and 0.4 μm. The diameters of the liposome preparations were measured by laser scattering in a LA-900 particle size distribution analyzer (Horiba, Irvine, Calif.), using the manufacturers method, except that the usual sonication step was omitted to avoid lysis (rupture) of the liposomes. Finally, to remove any unencapsulated dye, the liposomes were gel filtered on a 1×14 cm Sephadex G-50 column and dialyzed overnight against TBS at 4° C. When stored at 4° C., there was no significant leakage of dye over a period of 9 months as described below.

Sulforhodamine B was chosen as the dye for encapsulation, as described in O'Connell, above, and Chen, et al., *Anal. Biochem.*, 172 (1988) 61, hereby incorporated by reference, because of its fluorescence and high visible extinction coefficient. To prepare the dye, 20 mM Tris was used to buffer the dye solution. The pH was adjusted to 7.0 with NaOH to effect dissolution. The final solution contained 100 mM dye in 20 mM Tris at a pH of 7.0 with an osmolarity approximately equal to TBS, which was the buffer routinely used in all aqueous operations of the experiments. In some experiments 200 mM Sulforhodamine B was used to give a greater color intensity on the strips.

Because Sulforhodamine B is highly fluorescent and this fluorescence undergoes self-quenching when encapsulated, the integrity of the liposomes can be determined by measuring fluorescence intensity before and after lysis. Total and almost instantaneous lysis of the liposomes was effected by addition of a solution (final concentration=30 mM) of n-octyl-β-D-glucopyranoside at room temperature. For these fluorescence experiments, the dye was excited at a wavelength of 543 nm and fluorescence measured at the emission wavelength of 596 nm.

In some experiments the non-fluorescent dyes Isosulfan Blue and Fast Green FCF were encapsulated by the same methods as Sulforhodamine B.

Characteristics of liposomes

Liposomes were prepared by the reversed-phase evaporation method described in Szoka and O'Connell, above, but without extrusion through polycarbonate filters, giving a high yield of liposomes. However, these heterogeneously sized liposomes did not migrate evenly on the test strips used in the assay. This was improved by passing the preparations sequentially twice through each of two polycarbonate filters of 1.0 and 0.4 μm nominal pore diameter. Liposomes passed only through the 1.0 μm filter had a mean diameter of 1.82 μm, with a standard deviation of 0.8, while those passed through both filters had a mean diameter of 0.68 μm with a standard deviation of 0.12. This discrepancy between the size of the pores on the polycarbonate filters and the final size of the liposomes is not surprising, as the liposomes are very flexible, and can thus "squeeze" through a pore of smaller diameter. The liposomes of 0.68 μm diameter were a much more homogeneous population than those of 1.82 μm diameter, and both populations migrated more evenly on the nitrocellulose sheets than did the unextruded liposomes. Passing the preparation through an even smaller sized filter (0.2 μm) did not improve the migration behavior, and reduced the yield considerably. Consequently, liposomes that had been passed through the 1.0 and 0.4 μm filters were used in all subsequent experiments.

The absorption spectrum of dilute, free Sulforhodamine B gave a peak at 566 nm, with a shoulder at 532 nm. The intact liposomes, containing dye at a concentration sufficiently high to form dimers, as described in Chen, et al., *Anal. Biochem.*, 172 (1988) 61, hereby incorporated by reference, gave a spectrum with peaks at 532 and 568 nm, with the 568 nm peak at 70% of the height of the 532 nm peak. The addition of surfactant to the liposomes caused lysis of the liposomes and consequent dilution of the dye, and thus converted the spectrum to that of the free dye.

The presence of Alachlor on the surface of the liposomes was demonstrated by the reversal, by free Alachlor, of antibody-induced aggregation of the liposomes. The aggregated liposomes could be precipitated by centrifugation.

The liposomes were stored at 4° C., and the temporal stability was studied over time by measuring the percentage of free dye in the preparation, thereby allowing calculation of the percentage of the liposomes that had lysed.

The characteristics of the liposomes used in these studies are shown in Table I. From the size measurement results, it is possible to calculate that the average volume of a single liposome is $1.7 \times 10^{-10}$ μl. By assuming the dye encapsulated was equal in concentration to the original dye solution used, and by comparing the fluorescence of lysed liposomes to that of standard Sulforhodamine B solutions, it is possible to calculate that there were ca. $1.2 \times 10^8$ liposomes $\mu l^{-1}$ and that each liposome contained ca. $9.6 \times 10^6$ molecules of dye. Assuming that the average surface area of the DPPC molecules is 71 Å$^2$, and that of cholesterol molecules in a mixed bilayer is 19 Å$^2$, as described in Isaraelachvili, eta al., *Biochim. Biophys. Acta*, 389 (1975) 13, and given that the DPPE-Alachlor is 0.1 mole % of the total lip, there are ca. 3500 molecules of Alachlor on the outer surface of a single liposome.

TABLE I

| Liposome Characteristics | |
| --- | --- |
| Mean diameter (±S.D.) | $0.68 \pm 0.12$ μm |
| Volume | $1.7 \times 10^{-10}$ μl |
| Liposome conc. | $1.2 \times 10^{8}$ lipo μl$^{-1}$ |
| SRB$^a$ conc. | 100 mM |
| SRB$^a$ (molecular)$^b$ | $9.6 \times 10^{6}$ molec. lipo$^{-1}$ |
| Alachlor conc.$^c$ | $3.5 \times 10^{3}$ molec. lipo$^{-1}$ |
| Stability | >9 months |

$^a$Sulforhodamine B.
$^b$The number of molecules of SRB per liposome.
$^c$The number of molecules of Alachlor on the outer surface of a single liposome containing 0.1 mole % DPPE-Alachlor.

Example 2

Assay format

The assay device configuration consists of a wicking reagent containing Alachlor-tagged liposomes and a test strip comprised of a wick, an immobilized anti-Alachlor zone and an egg white avidin capture zone in sequence. The assay is performed by dispensing 100 μl (2 drops) of the sample or control solution and 50 μl (1 drop) of a three times concentrated TBS buffer into a 10×75 mm glass test tube, mixing the contents, and adding 50 μl (1 drop) of a liposome solution (stock liposome solution diluted 1:50, dilution varying according to preparation). The test tube is shaken mildly to mix the contents and the test strip is inserted into the tube; the strip is left in the tube until the solution front reaches the end of the strip (about 8 min); the strip is removed and air dried. The color intensity of the antibody zone and the egg white avidin zone are estimated either visually or by scanning densitometry, as described in Reeves, (1993).

The measurement of the extent of the competitive binding reactions of the analyte molecules and the tagged liposomes to the immobilized antibodies was optical. Visual estimation of the color intensity can be used, but for more accurate quantitation during development it was found to be preferable to use a computer scanner and Scan Analysis densitometry software (Biosoft, Ferguson, Mo.) to convert the red coloration into greyscale readings that can be measured.

A series of analyte determinations were made as described above with a series of Alachlor standards of varying concentrations. A decrease in color of the antibody zone with increasing concentrations of added Alachlor, and a concomitant increase in the color of the egg white avidin zone, was observed.

Figure 5:
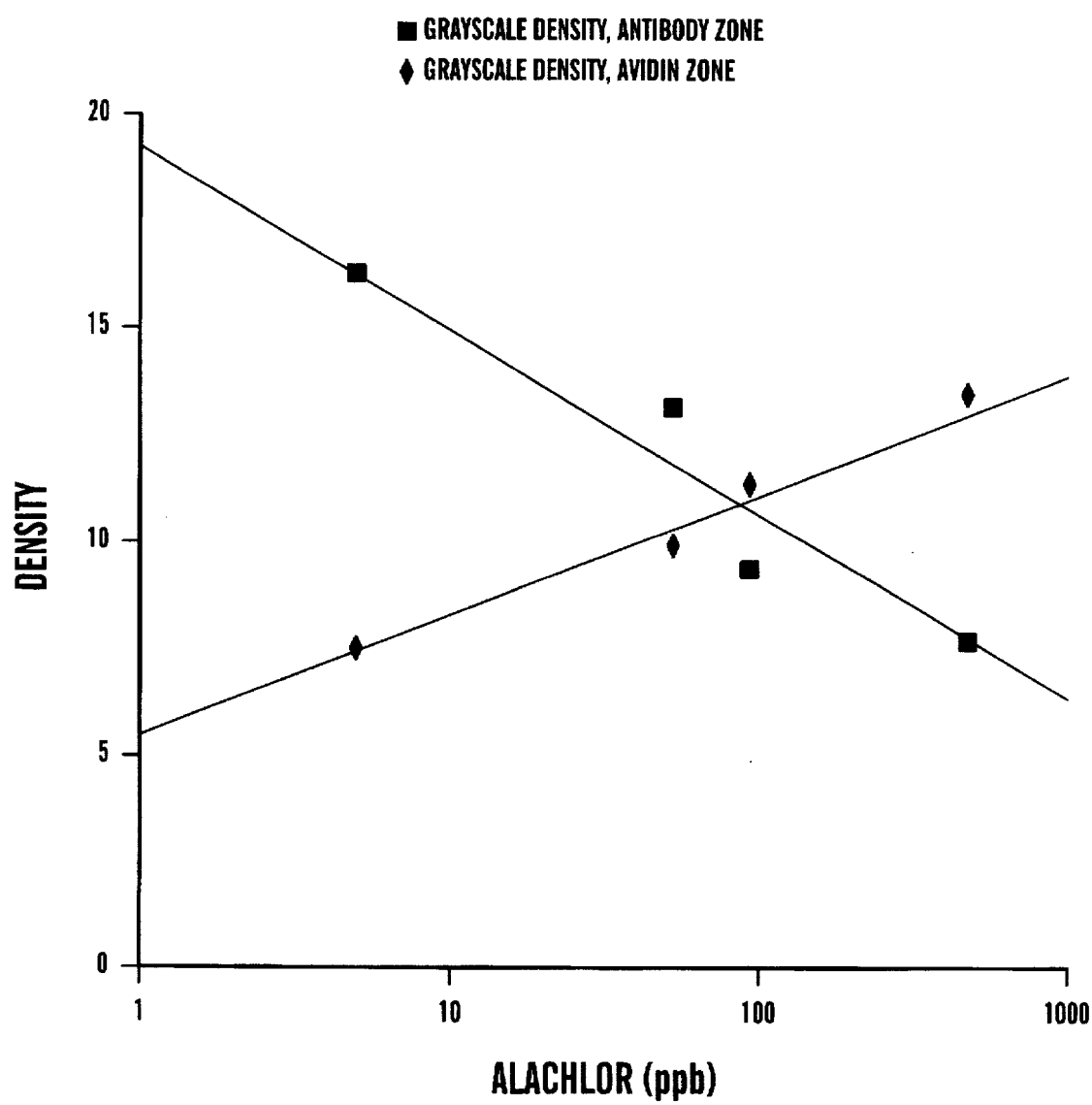
FIG. 5 is a plot of dose-response data obtained for samples containing various concentrations of Alachlor, as described in greater detail in Example 2, below.

Dose-response data obtained by scanning densitometry of strips run in the presence of various concentrations of Alachlor are shown in FIG. 5, which is a graph of greyscale density versus Alachlor concentration (ppb), measured in both the antibody and avidin zones.

The response in both the antibody and avidin zones varied logarithmically when measured using scanning densitometry, and both were estimated to be able to detect 5–10 μg/l Alachlor. When these strips were assessed visually, a similar determination could be made, but at low levels of added Alachlor it was somewhat easier to detect increases of red color over a white control (avidin zone) than decreases in color intensity (antibody zone).

Examples 3–9 illustrate the method of the invention, and preparation and use of the test devices in accordance with the invention, hereinafter referred to as the "liposome immunoaggregation" or "LIA" format for convenience. The LIA and LIC format are also illustrated together in the following examples.

Example 3

Materials for Examples 3–9

The materials employed in the remaining examples were as follows: Aroclor standards were purchased from Crescent Chemicals (Hauppauge, N.Y.) and 2-chlorobiphenyl (2ClBP) was purchased from Ultra Scientific (Kingstown, R.I.). N,N'-dicyclohexylcarbodiimide and N-hydroxysuccinimide were purchased from Pierce (Rockford, Ill.). Dipalmitoyl phosphatidyl ethanolamine (DPPE), cholesterol, Tween-20, triethylamine, tris (hydroxymethyl)aminomethane (Tris), Molybdenum Blue spray reagent, polyvinylpyrrolidone ($M_R$=40 kDa; PVP), gelatin (Type A: from porcine skin) and Sephadex G-50 were purchased from Sigma Chemical Co. (St. Louis, Mo.). Dipalmitoyl phosphatidyl choline (DPPC) and dipalmitoyl phosphatidyl glycerol (DPPG) were obtained from Avanti Polar Lipids, Inc. (Alabaster, Ala.). Biotin-x-DPPE was purchased from Molecular Probes (Eugene, Ore.), sulforhodamine B was purchased from Eastman Chemical Co. (Rochester, N.Y.), and Carnation non-fat dry milk powder (CNDM) was obtained locally. Protein assay dye reagent, goat anti-rabbit IgG alkaline phosphatase conjugate and the substrates for alkaline phosphatase were purchased from Bio-Rad Laboratories (Hercules, Calif.). Silica gel TLC flexible plates and preparatory silica gel plates, both containing fluorescent indicator, were obtained from Whatman (Maidstone, England). Plastic-backed nitrocellulose membranes with pore sizes >3 μm were obtained from Schleicher & Schuell, Inc. (Keene, N.H.). Caprylic acid (octanoic acid) was purchased from Aldrich (Milwaukee, Wis.). Soluble keyhold limpet hemocyanin (KLH) was purchased from Boehringer Mannheim Biochemical Products (Indianapolis, Ind.). The 2-chlorophenyl benzoic acid (2-ClPB) and rabbit anti-PCB IgG used in initial studies were supplied by the General Electric Corp. (Schenectady, N.Y.). Subsequent supplies of antiserum were produced at the Cornell University College of Veterinary Medicine, as described below. Anti-biotin antibodies were purchased from Whatman (Hillsboro, Ore.).

Example 4

Hapten Conjugations

The following reactions were modified from the procedure of Schmidt et al., Schmidt, D. J.; Clarkson, C. E.; Swanson, T. A.; Egger, M. L.; Carlson, R. E.; Van Emon, J. M.; Karu, A. E. *J. Agric, Food Chem.* 1990, 38, 1763–1770, which is hereby incorporated by reference. Twenty μmol of 2ClPB were activated overnight in a small volume (approx. 1 mL) of 1:1 chloroform:methanol with 40 μmol N,N'-dicyclohexylcarbodiimide (DCC) and 40 μmol N-hydroxysuccinimide (NHS) while stirring at room temperature. This solution was split into two vials, evaporated to dryness, and lipid or protein solution was added as described below.

Five mg DPPE were dissolved in 0.9 mL chloroform with a 0.7% triethylamine at 45° C. This solution was then added to one half of the activated 2ClPB and stirred at 45° C. overnight. Confirmation of the successful conjugation reaction was achieved by a combined thin-layer chromatographic and an enzyme immunostaining method, as described in Mattsby-Baltzer, I; Alving, C. R. Euro. *J. Biochem.* 1984, 138, 333–337, hereby incorporated by reference using an anti-2ClPB antibody supplied by the General Electric Corporation. The presence of 2ClPB-DPPE was confirmed by the appearance of a purple spot for the 2ClPB with enzyme immunostaining and by a blue one with the chromatographic analysis, indicating the presence of phospholipid. This indicated both 2ClPB and DPPE at the same Rf value, which was different from the Rf of the two starting materials, and therefore a new reaction product, i.e., the DPPE-2ClPB conjugation product.

KLH (0.333 µmol) was dissolved in 2 mL of 0.1M NaHCO$_3$ buffer (pH=8.5). One half of the activated 2ClPB was dissolved in 0.5 mL dimethylformamide (DMF) and then added dropwise to the KLH solution over 20 minutes. The pH was maintained at 8.5 for the next 4 hours, and the solution was stirred overnight at 4° C.

Successful immunogen conjugation was confirmed by LIA analysis. Twenty µg of the DPPE-2ClPB conjugation product were added to 75 µL solutions, containing $1.3 \times 10^4$ 2ClPB-tagged liposomes µl$^{-1}$ (preparation described below in Example 6), and 30 picomoles purified anti-PCB antibody. The solution was shaken briefly and then incubated for 15 minutes. LIA sensor strips, discussed below, were then inserted and the solvent front was allowed to reach the top of the strip before removal. The strips were air dried and then observed visually. Sensors dipped into KLH control solutions displayed a dark aggregation zone and those dipped into solutions containing the supposed 2ClPB-KLH showed no aggregation. This demonstrated complete aggregate inhibition by the 2ClPB-KLH and indicated a successful conjugation product.

Example 5

Antibody Production

Antibodies to the immunogenic conjugation product were raised in two New Zealand white rabbits at the Cornell College of Veterinary Medicine. The IgG fraction was purified from antisera by the caprylic acid/ammonium sulfate precipitation method, described in McKinney, M. M.; Parkinson, A. *J. Immunol. Methods* 1987, 96, 271–279, which is hereby incorporated by reference. Antibodies obtained in this manner were used in all subsequent studies.

Example 6

Preparation of Dye-Encapsulated PCB-Tagged Liposomes

Sulforhodamine B was dissolved in 20 mM Tris, pH 7.0, to a final concentration of 200 mM. Because sulforhodamine B is highly fluorescent and this fluorescence undergoes self-quenching when encapsulated, the integrity of the liposomes can be determined by measuring fluorescence intensity before and after lysis. All liposome preparations demonstrated greater than a twenty-fold increase in fluorescence after lysis. Total and almost instantaneous lysis of the liposomes was effected by addition of a solution (final concentration=30 mM) of n-octyl-β-D-glucopyranoside at room temperature. For these fluorescence experiments, the dye was excited at 543 nm and the emission was measured at 596 nm.

Liposomes were designed to be competitive markers in an immunoassay for polychlorinated biphenyls (PCB), and this was accomplished by incorporating previously coupled 2ClPB-DPPE into liposome bilayers by the reverse-phase evaporation method described in Siebert, T. A.; Reeves, S. G.; Durst, R. A. *Anal. Chim. Acta* 1993, 282, 297–305, hereby incorporated by reference, from a mixture of DPPC, cholesterol, DPPG, 2ClPBDPPE conjugate, and biotin-x-DPPE in a molar ratio of 5:5:0.5:0.1:0.01. The mean diameter of liposomes, prepared as described, was measured by laser diffraction particle size analysis in a Coulter LS 130 instrument (Coulter Corporation, Hialeah, Fla.), using the manufacturer's method.

Example 7

Time Course Measurements of Liposome Immunoaggregation

Fifteen mL solutions were made containing 0 or 100 ppb Aroclor 1232 and $1.8 \times 10^4$ liposomes µL$^{-1}$ in Tris buffered saline (TBS), pH 7.0 with 10% methanol. The liposome concentration was increased over what is routinely used in the LIA assay ($1.3 \times 10^4$ liposomes µL$^{-1}$) in order to provide enough obscuration for measurements to be taken. The solution was stirred for 30 s in the microfluid module of the Coulter LS 130. The stirrer was stopped and particle sizes measured by laser diffraction for 60 s, according to the manufacturer's instructions. The liposome solution was then decanted from the module into a glass beaker. Anti-PCB antibody (6 nmol) was then dispensed into the empty fluid module and the liposome solution was added back, in order to insure thorough mixing. Particle size measurements were taken over 60 s intervals for up to 25 min.

Example 8

Preparation of LIC and LIA Sensor Strips

Nitrocellulose membrane was cut into 8×15 cm sheets, thoroughly wetted with 10% methanolic TBS, pH 7.0, and dried under vacuum. The membrane sheet was mounted on a Linomat IV (CAMAG Scientific Inc., Wrightville Beach, N.C.) microprocessor controlled TLC sample applicator. Solutions of anti-PCB antibodies (0.2 mg mL$^{-1}$) and anti-biotin antibodies (0.5 mg mL$^{-1}$) were applied at 1.25 µL s$^{-1}$, for 85 s, with 190 kPa (27.5 psi) N$_2$ producing anti-biotin zones as shown in FIGS. 8A and 8B and anti-PCB zones as shown in FIG. 8A. This equates to 4.1 and 10 picomoles of anti-PCB and anti-biotin antibodies, respectively, per 5 mm strip. Sheets were then vacuum dried for 1.5 h. The coated nitrocellulose sheet was then immersed in the blocking agent (0.25–0.75% gelatin, 0.02% PVP, 0.005% CNDM, 0.002% Tween-20) for 1 h on a rotating mixer and dried under vacuum for 3–4 h. Prepared sheets were cut into 5×80 mm strips and stored in the presences of silica gel desiccant at either room temperature at 4° C. until ready for use.

Example 9

Assay Protocol

The format for the LIC assay, shown in FIG. 8A, consists of a solution containing PCB-tagged liposomes and a nitrocellulose test strip with immobilized anti-PCB and antibiotin capture zones in sequence. The LIC assay is performed by dispensing 25 µL of the sample (in water or up to 30% methanol extraction solvent) and 25 µL of a 3 times concentrated solution of TBS buffer into a 10×75 mm glass test tube, mixing the contents, and adding 25 µL of a liposome solution (stock liposome solution diluted to $3.9 \times 10^4$ liposomes µL$^{-1}$).

The format for the LIA assay, shown in FIG. 8B, is modified by adding 30 picomoles of anti-PCB antibody/drop to the concentrated TBS solution. Furthermore, after mixing, the solution is allowed to incubate at room temperature for 15 minutes before continuing with the assay. After these initial preparations the test tube is shaken mildly to mix the contents and the test strip is inserted. In both formats, the strip is left in the tube until the solution front reaches the end of the strip (ca. 8 min); the strip is then removed and air dried. The color intensity of all zones is estimated visually or by scanning densitometry. Visual estimation of the color intensity can be used, but for more accurate quantitation it was found to be preferable to use a desktop scanner (Hewlett Packard Scan Jet IIc, Palo Alto, Calif.), and Scan analysis densitometry software (Biosoft, Ferguson, Mo.) to convert the red coloration into greyscale readings.

All calibration and other experiments followed the above protocols. For the construction of calibration curves, blank solutions were run into quadruplicate and all calibrant solutions were run in triplicate. Both the LIC and LIA curves were constructed with 6 data points spanning the dynamic range.

The LIC format has two immobilized reagent zones, shown in FIG. 8A. Buffered solutions containing liposomes and various amounts of PCBs migrate vertically through channels in the nitrocellulose polymer matrix by capillary action and sequentially pass through the competition and measurement zones. FIG. 8A depicts the competitive binding events that occur on the surface of the nitrocellulose during LIC. It should be emphasized that this reaction occurs in a flowing solution and is therefore under non-equilibrium conditions. Initial experiments have shown that the ratio of liposome binding at the two zones remains constant despite changes in the liposome concentration over two orders of magnitude. Only the absolute signal intensity changed in these experiments. Many of the binding sites in the antibody zone are likely to be unavailable due to the random orientation of adsorbed antibodies and possibly to some loss of activity during the blocking and drying steps in the sensors preparation. See Brown, W. R.; Dierks, S. E.; Butler, J. E.; Gershoni, J. M. In *immunochemistry of solid-phase immunoassay;* J. E. Butler, Ed.; CRC Press, Inc.: Boca Raton, 1991; 151–172. A range of antibody concentrations, quantified by total protein analysis of the purified anti-PCB, was tested and it was observed that higher sensitivity could be achieved by applying smaller amounts of antibody (data not shown). However, the color intensity quickly became so light that results were not visually quantifiable. Therefore, an optimal 4.1 picomoles antibody/sensor were used for LIC analysis in subsequent experiments. Accordingly, the antibody competition zone will display an inverse relationship to the amount of analyte present. A second zone of antibiotin is applied, at a high enough concentration (11.9 picomoles/sensor), to capture all liposomes that escape binding in the competition zone at maximal inhibition from analyte. This zone displays a proportional relationship between color intensity and analyte concentration.

The LIA format consists of a homogeneous aggregation reaction, migration on a nitrocellulose sensor, and detection in an immobilized anti-biotin capture zone, as shown in FIG. 8B. During migration, all liposome particles must move through a tortuous path in the nitrocellulose matrix. In doing so, large particle sizes will tend to be retained in the interstices and will form the aggregation zone. Smaller particle sizes will not be inhibited and will continue to migrate until bound in the anti-biotin collection zone. Upon mixing, the bivalent IgG and multi-haptenated liposomes ($5.4 \times 10^4$ molecules liposome$^{-1}$) undergo multiple crosslinking events, as depicted in FIG. 9A. The resulting multi-liposome structures are similar to those reported for avidin/biotin induced liposome aggregation in Chiruvolu, S.; Walker, S.; Israelachvili, J.; Schmitt, J.-J.; Leckband, D.; Zasadzinski, J. A. *Science* 1994, 264, 1753–1756, hereby incorporated by reference. By occupying antibody binding sites, PCBs inhibit aggregation, and an inversely proportional signal will be displayed at the aggregation zone, which forms at the meniscus of the test solution in which the test device is inserted. The liposomes that do not aggregate will be proportional to the amount of analyte in solution and bind to the measurement zone as described for the LIC sensor. An advantage of the LIA format over the LIC format is that the competitive reaction is allowed to more closely approach equilibrium during the incubation period and thus achieves higher sensitivity. Furthermore, no analyte-specific antibody is immobilized on the nitrocellulose. With only the measurement zone remaining, the LIA strips become a generic immunoassay component that can be used with any suitable incubation reaction.

The two formats presented consist of an inversely proportional and a directly proportional zone where signal intensity can be measured. The lower, inversely proportional zone of each type of sensor will be referred to here as the reaction or R zone because of its close relationship with the competitive binding events between liposomes and antibody. The higher, directly proportional zone will be referred to as the collection or C zone, which indicates that this zone only serves to accumulate liposomes not retained in the reaction zone due to the presence of analyte.

The analyte analog-tagged liposomes proved to be quite robust reagents. Liposome stock solutions were stored at 4° C., in the dark, and were essentially 100% intact after 7 months of storage. This is in agreement with other reports which have also noted quite stable liposome preparations with storage at 4° C. Plant, A. L.; Brizgys, M. V.; Locascio-Brown, L.; Durst, R. A. *Anal Biochem* 1989, 176, 420–426; Pinnaduwage, P.; Huang, L. *Biochemistry* 1992, 31, 2850–2855; Babbitt, B.; Burtis, L.; Dentinger, P.; Constantinides, P.; Hillis, L.; Mcgirl, B.; Huang, L. *Bioconjugate Chem* 1993, 4, 199–205; Siebert, T. A.; Reeves, S. G.; Durst, R. A. *Anal. Chim. Acta* 1993, 282, 297–305; each of which is hereby incorporated by reference. One report states that liposomes showed 100% stability for one year at room temperature. Plant, A. L.; Brizgys, M. V.; Locascio-Brown, L.; Durst, R. A. *Anal Biochem* 1989, 176, 420–426. PCB-tagged liposomes could also be left at room temperature for one month without any significant loss of encapsulant and studies are ongoing to determine if this can be extended to one year as noted by others.

The characteristics of the liposomes prepared as described in Example 6 are listed in Table II. The mean diameter is slightly smaller than reported previously, Siebert, T. A.; Reeves, S. G.; Durst, R. A. *Anal. Chim. Acta* 1993, 282, 297–305. However, three significant changes have been made: the entrapped dye was increased two-fold to 200 mM, DPPE-biotin was incorporated, and the total amount of analyte-DPPE was increased ten-fold to 1 mole %. These changes could account for the formation of liposomes with slightly different characteristics. See *Liposomes: A Practical Approach;* New, R. R. C., Ed.; Oxford University Press: New York, 1990, 301, hereby incorporated by reference. From the size measurements, it was possible to calculate the mean volume of a single liposome and all subsequent calculations were performed as previously described. Siebert, T. A.; Reeves, S. G.; Durst, R. A. *Anal. Chim. Acta* 1993, 282,297–305.

TABLE II

| PCB-tagged liposome characteristics[a] | |
| --- | --- |
| Mean diameter (±1 S.D.) | 0.61 ± 0.18 μm |
| Volume | $1.19 \times 10^{-10}$ μL$^{-1}$ |
| Liposome conc. | $1.33 \times 10^6$ liposomes μL$^{-1}$ |
| SRB conc., liposomal | 200 mM |
| SRB content | $1.4 \times 10^7$ molecules liposome$^{-1}$ |
| Hapten surface density (1 mole %) | $5.4 \times 10^4$ molecules liposome$^{-1}$ |
| Biotin surface density (0.1 mole %) | $5.4 \times 10^3$ molecules liposome$^{-1}$ |
| Stability | >1 year |

[a]Measurements performed on liposomes stored at 4° C. in TBS.

The proper concentration of liposomes to be used in the immunomigration assays was determined by establishing two initial criteria: in either format, the collection (i.e., measurement) zone (C) must provide a greyscale density reading of at least 7.500 (arbitrary units), and the ratio of the reaction zone (R) (competitive binding portion in LIC format; aggregation zone in LIA) to the capture zone (R/C) must be less than or equal to 1, at an analyte concentration that causes maximal inhibition. These two criteria insure that the signal intensity will be visually obvious and that greater than 50% of the liposomes that could potentially accumulate in the R zone will be released to the C zone. A liposome concentration of $1.3 \times 10^4$ liposomes μL$^{-1}$ was observed to give a C-zone greyscale reading of 10.325 arbitrary units for the LIA and 8.916 for the LIC formats. This liposome concentration also provided a R/C of 0.72 and 0.51 for the LIC and LIA, respectively, after addition of 10 nanomoles of Aroclor 1232. If the total signal is summed for the R and C zones and considered to present 100% of the liposomes available for detection, then the R/C ratio can be used to determine the percentage that is associated with each individual zone. Therefore, 58.2% and 66.2% of the liposomes, for LIC and LIA, respectively, were released to the C zone at maximal inhibition from Aroclor 1232. This satisfied our criteria and all subsequent experiments were carried out at this liposome concentration.

Example 10

Liposome Stability in Methanol

Figure 10:
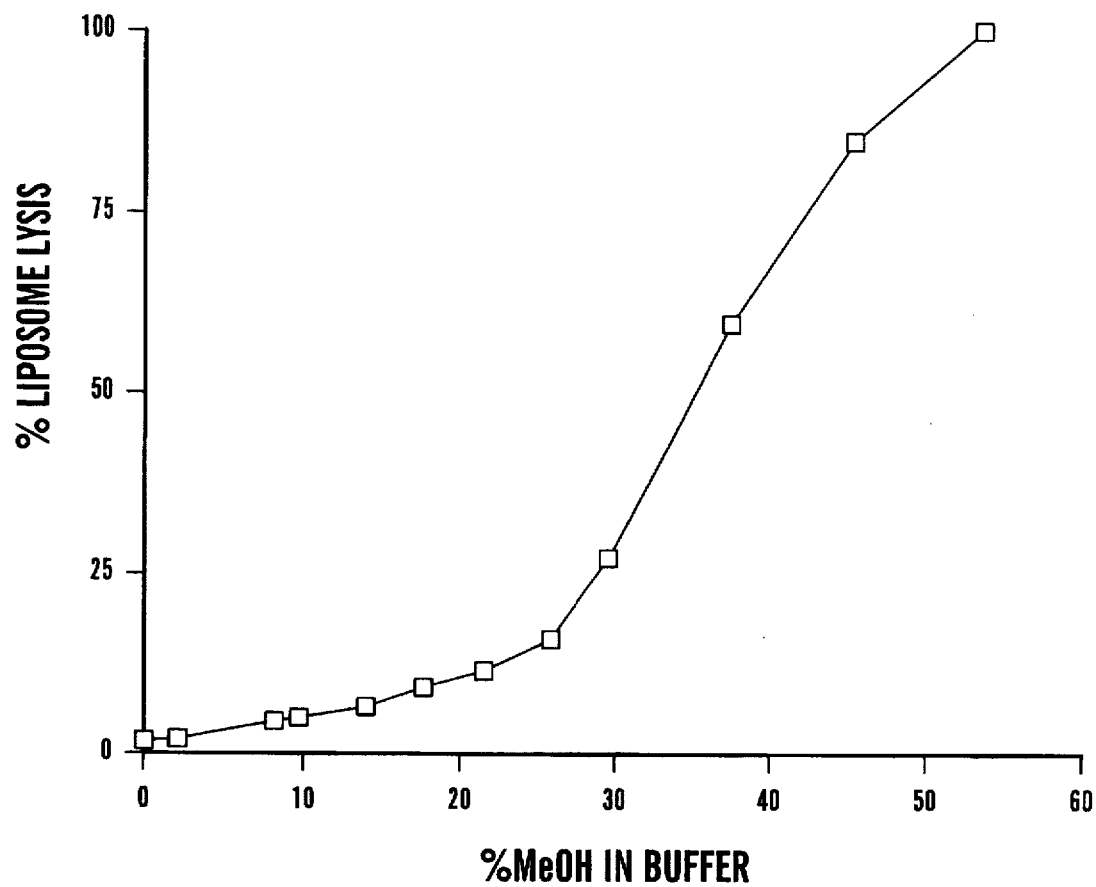
FIG. 10 is a plot of percent liposome lysis vs. methanol concentration, as described in greater detail in Example 10, below.

A number of the commercially available PCB immunoassays use a simple methanol extraction procedure when testing for PCBs in soil or from wipe tests. Therefore, the effect of methanol on the stability of liposomes was studied. The criterion for the establishment of an allowable concentration of methanol in our assay was set at 5% lysis or less. FIG. 10 displays a dose-response curve for an increasing percentage of methanol in TBS. The solvent resistance of liposomes is evident from these data as nearly 75% of liposomes are resistant to methanol concentration up to 30% of the assay buffer. A 10% methanolic buffer produced 5.2% lysis and was deemed acceptable. All lysis occurred within the first two minutes after liposome addition. The absence of a time-dependent effect indicates that the liposomes are differentially susceptible to lysis by methanol. If all liposomes were of equal stability, then a given exposure time should lyse a certain percentage of liposomes, and continuing exposure would cause continual lysis until the solution was cleared of intact liposomes. These data indicate that whatever percentage of the population is susceptible to a given amount of methanol, lyse immediately, and the remaining population is resistant over the time period of the experiment.

If methanol differentially affects subpopulations of liposomes, then it should be possible to observe a change in the liposome size distribution upon exposure. Table III lists the percentage of liposomes that are greater than a given particle size after exposure to methanol. For all particle sizes measured, exposure to an increasingly methanolic buffer results in an increase in the population percentage, this indicates that methanol exposure may preferentially lyse smaller diameter liposomes, i.e., <0.5 μm, and thereby increase the relative percentage of larger diameter liposomes. One report has noted that increasing amounts of short-chain alcohols, including methanol, induce a transition in DPPC from the bilayer gel to the interdigitated state. This is accompanied by an increase in the mobility of the phospholipid head group and a decrease in the stability of the liposomes. See Liposomes, A. Practical Approach; New, R. R. C., ed.; Oxford University Press: New York 1990. See Herold, L. L.; Rowe, E. S.; Khalifah, R. G. Chem Phys Lipids 1987, 43, 215–226, hereby incorporated by reference. This study did not investigate effects on different sized liposomes, but due to the higher strain already present on smaller diameter liposome bilayers (see Chiruvolu, S.; Walker, S.; Israelachvili, J.; Schmitt, F.-J; Leckband, D.; Zasadzinski, J. A. Science 1994, 264, 1753–1756, hereby incorporated by reference), this solvent effect may be more pronounced at these sizes. Because it is the small diameter liposomes that contribute to the background signal observed at the C zone, a 10% methanolic buffer should reduce the number of these liposomes by destabilization and lysis, thereby improving the signal to noise ratio of the assay. A 10% methanolic buffer was used in all subsequent experiments and has been determined to be a reasonable concentration for the extraction solvent.

TABLE III

| | Effect of extraction solvent on liposomal size characteristics. | | |
| --- | --- | --- | --- |
| Particle | % MeOH | | |
| Diameter (μm) | 1% %> | 5% Diameter[a] | 10% |
| 0.50 | 67.13 | 68.03 | 68.46 |
| 0.75 | 14.85 | 17.92 | 18.66 |
| 1.00 | 02.01 | 03.88 | 04.36 |
| 2.00 | 00.03 | 00.05 | 00.10 |
| 5.00 | 00.01 | 00.01 | 00.02 |

[a]Indicates number % of liposomes > the particle diameter listed.

As discussed, the color intensities in the R and C zones in the LIA assay are indicators of the number of associations between liposomes and anti-PCB antibodies. With increasing concentrations of analyte, this association is increasingly inhibited and a lower color intensity will result in the R zone. However, in the absence of analyte, the color intensity observed in these zones is directly related to the binding strength between liposomes and antibody: if aggregation increases, then a higher binding affinity is indicated, as noted in Katoh, S.; Mori, Y.; Fujita, R.; Sada, E.; Kishimura, M.; Fukuda, H. Biotechnology and Bioengineering 1993, 41, 862–867, hereby incorporated by reference. In this sense, the R and C zones are somewhat analogous to the measurements of antibody-bound and free analyte that are used in a Scatchard analysis for the determination of affinity constants for receptors and their ligands. See Scatchard, G. Ann. N.Y. Acad. Sci, 1949, 660–672, hereby incorporated by reference. In a Scatchard analysis, the ratio bound/free analyte is plotted as a function of the amount of analyte bound, and the slope of this plot equals the affinity constant. The strip is, in essence, acting to separate those liposomes which have not been bound by antibody from those which have. The reason this device cannot be used for the exact determination of affinity constants is that the R zone intensity is actually produced by large aggregates resulting from numerous multiple binding events and likewise the C zone intensity is most probably produced by free liposomes and small aggregates. Thus a detailed Scatchard analysis using LIA is not able to provide an affinity (or avidity) constant in the traditional sense. However, the device can be used to compare relative antibody affinities and provide useful information for the selection of antibodies within the context of the liposome-based immunoassays.

Antisera from two different rabbits were analyzed for their liposome binding ability as a way to determine their suitability for use in the further development of immunomigration PCB assays. Thirty nanomoles of either antibody preparation (identified below as #1 and #2) were added to liposome solutions, without PCBs, and incubated for 15 minutes according to the standard LIA protocol. Antibody #1 displayed a R/C of 4.16 and antibody #2 displayed a R/C of 60.9. These ratios indicate that 81% and 98% of available liposomes, for antibody #1 and #2 respectively, are bound in the R zone. On this basis, antibody #2 was chosen for its high R/C ratio which indicates its greater ability to induce immunoaggregation of PCB-tagged liposomes. Furthermore, the small C zone signal produced with antibody #2 was desired in order to minimize the background signal for blank solutions.

Figure 11:
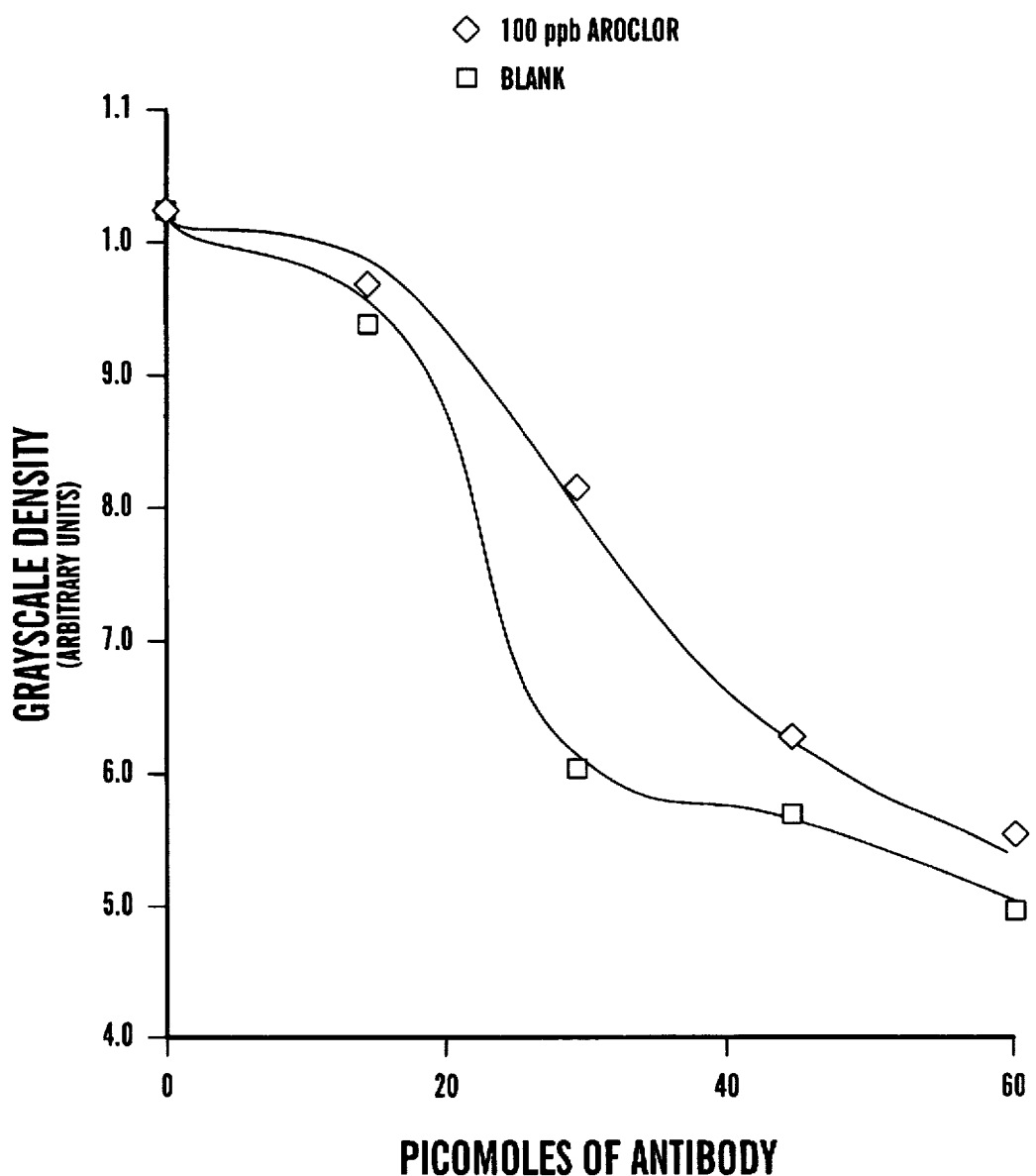
FIG. 11 is a plot of grayscale density vs. picomoles of antibody in solutions containing 0 and 100 ppb Aroclor as described in greater detail following the Examples, below.

Varying amounts of antibody #2 were tested using LIA in order to determine the optimal amount of antibody to be used during the incubation step. At each level, LIA was performed with solutions containing zero and 27 picomoles of Aroclor 1232. The greyscale density at the C zone was measured and is displayed in FIG. 11. Antibody amounts lower than 20 picomoles induced very little aggregation and therefore only a small signal change was observed with the addition of PCBs. At higher antibody levels, aggregation was more complete but, again, only a small signal change was observed upon addition of PCBs. These levels present too many PCB binding sites and can readily bind both analyte and PCB-tagged liposomes without inhibiting immunoaggregation. Thirty nanomoles of antibody #2 displayed the largest signal difference between the blank and PCB solutions and, therefore, was used for all subsequent experiments.

Several forces can act to induce liposome aggregation, including van der Waals, ion-binding, hydrophobic interactions, depletion forces, and receptor-ligand interactions, as described in Chiruvolu, S.; Walker, S.; Israelachvili, J.; Schmitt, J.-J.; Leckband, D.; Zasadzinski, J. A. *Science* 1994, 264, 1753–1756, hereby incorporated by reference. The receptor-ligand interactions are the only forces that can be considered to induce specific aggregation since they only act at specific points on the liposome surface and only when the interacting molecules are present. This form of aggregation produces little deformation or stress on bound liposomes in contrast to the other more non-specific forces, which are often associated with increased fragility, lysis, and fusion. None of the liposome preparations described herein exhibited aggregation before the introduction of anti-PCB antibody. Liposome preparations were observed for six months and showed no increase in the mean liposome diameter, indicating that non-specific aggregation forces do not interfere with the immunoaggregation assay.

Figure 12:
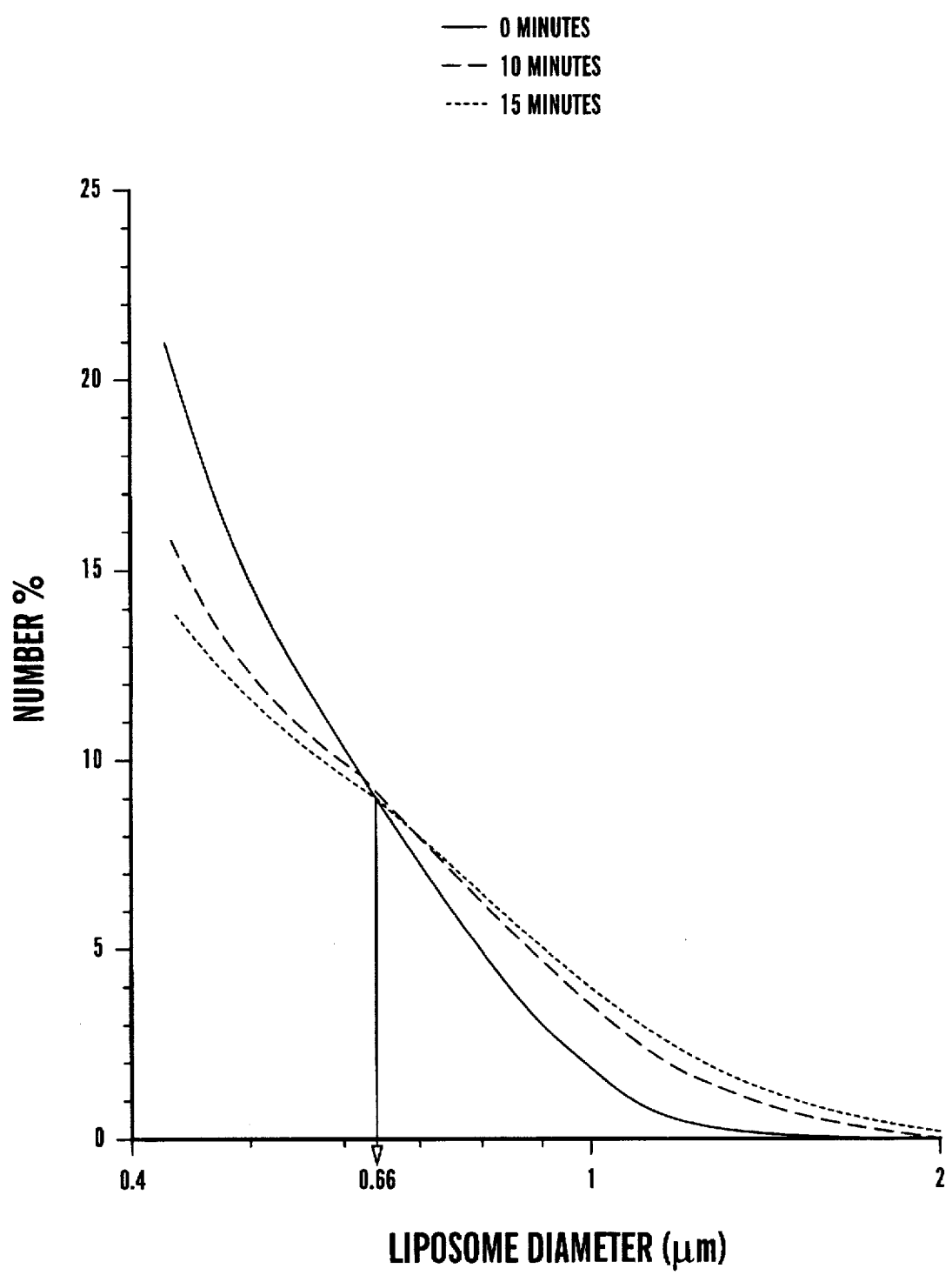
FIG. 12 is a plot of the results of a laser diffraction analysis of liposome immunoaggregation over time, as described in greater detail following the Examples, below.

The time-dependent development of liposome-antibody aggregates was investigated using laser diffraction particle size analysis and is shown in FIG. 12. The liposome size distribution, observed before addition of antibody (at t=0), displays a size distribution with a large number of small diameter liposomes and is typical of intermediate-sized unilamellar vesicle (IUV) preparations. See *Liposomes: A Practical Approach;* New, R. R. C., Ed.; Oxford University Press: New York, 1990, hereby incorporated by reference. After the addition of antibody, the percentage of smaller liposomes can be seen to decrease and that of the larger diameters to increase. The liposome size distribution continues to change with time and all distributions pass through a point at 0.66 µm. All of the size distributions decrease essentially to zero % above a diameter of two microns.

The point at which the distributions converge indicates that the number of particles having less than a 0.66 µm diameter are decreasing and that the number of greater diameter particles is increasing, as a percentage of the size distribution. This also indicates that any particles having diameters smaller than 0.4 µm do not contribute significantly to the immunoaggregation. If these particles were present in great concentration and aggregating significantly, they would quickly become visible over time, as the multi-liposome aggregates grew beyond a 0.4 µm diameter. It would then be expected than an increase in liposomes near 0.4 µm would be observed over time, however, FIG. 12 clearly demonstrates a decrease in this area.

This point of convergence is very close to the mean diameter of the stock liposome preparation. Liposomes of this size begin to change immediately after the introduction of antibody and therefore could set the convergence point that is subsequently observed. Small particles form aggregates that increase towards the initial mean size, while particles with diameters greater than or equal to the initial mean, continue to aggregate to even larger sizes. Therefore the initial mean could be a point for the size distribution to shift through over the course of immunoaggregation, assuming that the rate of aggregation is the same for smaller particles as it is for the larger ones. These data would indicate that 0.66 µm aggregates are being formed at roughly the same rate that they grow into larger diameter sizes, however the fundamental significance of this value is unclear at the present time.

Figure 13C:
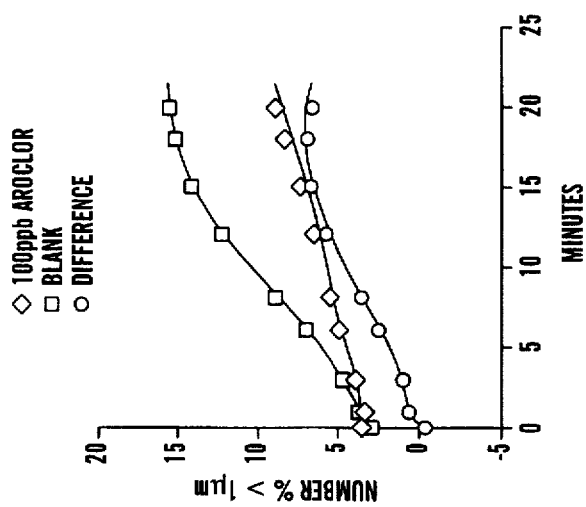
FIGS. 13A–13C illustrates PCE inhibition of liposome immunoaggregation.

Obscuration is a measurement of solution turbidity and will increase with an immunoaggregation induced increase in particles sizes. See Collord, B. C.; Marchal, E.; Humbert, G.; Linden, G.; Montagne, P.; El-Bari, N.; Duheille, J.; Varcin, P. J. *Dairy Sci* 1991, 74, 3695–3701, hereby incorporated by reference. Sample obscuration is especially useful for comparing liposomes of identical composition and concentration for relative changes in the entire size distribution. See *Liposomes: A Practical Approach;* New, R. R. C., Ed.; Oxford University Press: New York, 1990, 301, hereby incorporated by reference. FIG. 13A illustrates the time-dependent increase in laser light obscuration observed for liposome solutions containing 0 and 100 ppb of Aroclor 1232. The 100 ppb solutions correspond to 27 picomoles of Aroclor 1232 per test. Both solutions aggregated following logarithmic trends which demonstrates that, while both solutions continue to increase in their mean size, the aggregation begins very rapidly. This study also shows that a significant inhibition of liposome immunoaggregation with 100 ppb of PCBs reaches a maximum between 5 and 20 minutes.

Figure 13B:
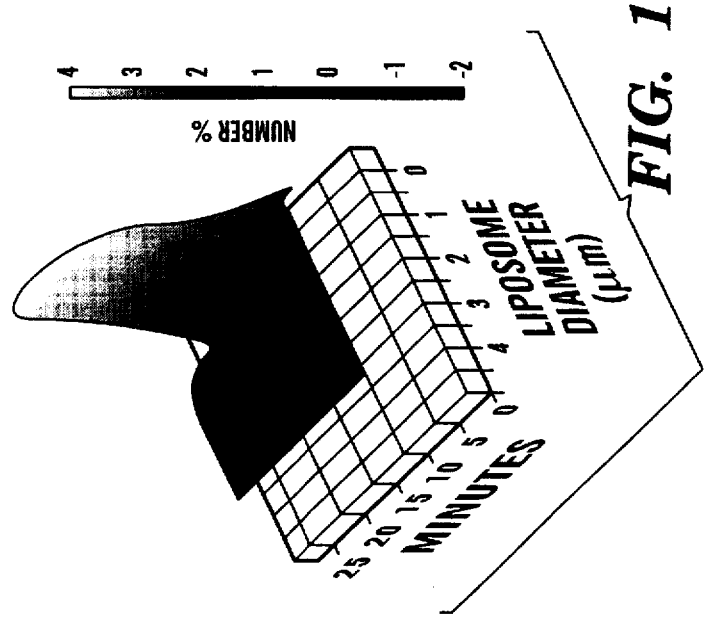
Figure 13A:
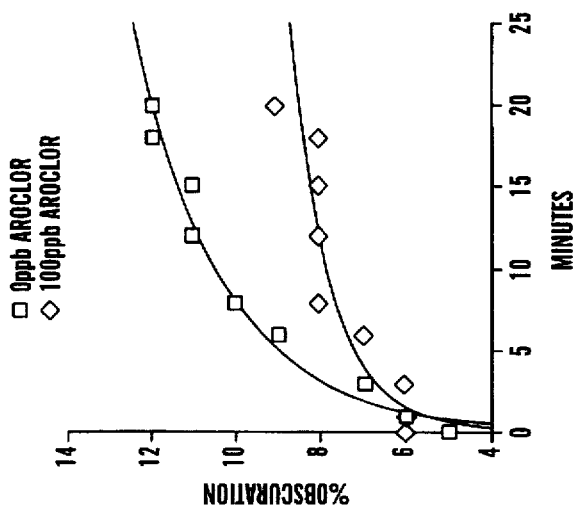

More information may be obtained from analysis of all particle information at each time point, as shown in FIG. 13B. The z axis is the observed percentage difference in the liposome size distribution with the blank solution being subtracted from the 100 ppb PCB solution. Therefore, in this analysis, positive percentage differences indicate a greater number percentage in the PCB solution and negative differences indicate a greater percentage in the blank solution. An increasing percentage difference in small diameter particles is the most obvious trend, indicated by the tall peak located at the very smallest (<0.66 µm) liposome diameters. These data demonstrate that small liposome particles are not aggregating appreciably in a PCB containing solution when compared to similarly sized particles in a control solution. It should also be noted that this peak begins to level off between the 10 and 15 minute time points. Therefore after a fifteen minute incubation step, PCB-containing solutions will retain a large percentage of liposomes of small diameters and would be expected to contribute to a higher C zone signal. As is demonstrated later, increases in PCB concentration causes a corresponding increase in the observed C zone signal.

The second trend to be noted is the trough formed at diameters between 0.66 and 2 µm, and which has a mode of 1 µm. This trough begins around 5 minutes and is level at about 15 minutes. This trend indicates that particles of this subgroup increase with time in the blank over the PCB-containing solutions. These data correlate well with the obscuration data as no significant difference can be seen before 5 minutes, and that the difference is essentially level by 15 minutes. The particle size range composing the trough is expected to contribute to the high R zone signal that is observed with blank solutions.

In order to more carefully define the aggregation that is thought to directly contribute to color intensity at the R zone, the number percentage of large diameter particles was measured. Particles with diameters close to 1 µm were shown to comprise the largest difference between blank and PCB-containing solutions (FIG. 13B; trough with mode of 1 µm). These particles are of the size expected to be migrationally inhibited on the nitrocellulose strips, as indicated in FIG. 13B, and thus contribute to the high R zone signal associated with PCB-free solutions. The results shown in FIG. 13C are in agreement with obscuration measurements demonstrating trends toward increasing immunoaggregation with time. The difference between the two curves is plotted and demonstrates the optimal incubation time as being 15 minutes. This is the period when the difference curve levels off completely and would be expected to be the least influenced by differences in the incubation time. Therefore, subsequent experiments were performed with a 15 minute incubation step in order to minimize operator error and to make timing decisions less critical to obtaining reproducible results.

The need for adequate blocking reagents used in nitrocellulose-based reactions has been demonstrated previously. See Rocha; Lee, R. F.; Niblett, C. L. *J Virol Methods* 1991, 34, 297–309; Batteiger, B.; Newhall, W. J.; Jones, R. B. *J. Immunol. Methods* 1982, 55, 297–307; and Johnson, D. A.; Gautsch, J. W.; Sportsman, J. R.; Elder, J. H. *Gene Anal Techn* 1984, 1, 3–8, each of which is hereby incorporated by reference. Initial experiments had shown the need to block the nitrocellulose because liposomes would not migrate past the meniscus on unblocked strips. Since our test is intended to be read visually, the need to maintain a low background on the strips is critical to the observation of small differences in color intensity. Several methods of blocking were initially examined, however, solutions containing gelatin as the chief blocking reagent demonstrated the highest uniformity at both the background and binding zone areas of the strips. The data in Table IV indicate that liposome migration is proceeding, however, as the gelatin content of the blocking solution is increased, the amount of liposomes that nonspecifically bind to the nitrocellulose also increases. It should also be noted that, with increasing amounts of gelatin, the migration time is increased. This indicates a reduction in the capillary force which may be due to gelatin blockage of the small interstices within the nitrocellulose matrix. Therefore, 0.25% gelatin blocking was chosen for its ability to allow fast liposome migration and yet maintain a nonspecific background signal close to the ideal nitrocellulose surface to which no liposomes have been applied. Concentrations of gelatin lower than 0.25% in the blocking solution were not expected to significantly improve the assay as solvent migration time was already equal to a non-blocked strip.

TABLE IV

Effect of gelatin blocking on non-specific liposome binding and overall assay migration time.

| % Gelatin in Blocking Solution | Background Signal O.D. | Migration Time Minutes |
|---|---|---|
| 0.00 | 2.533 | 7.75 |
| 0.25 | 3.253 | 7.72 |
| 0.50 | 3.678 | 8.15 |
| 0.75 | 3.999 | 9.93 |

Confidence intervals are not commonly used in determining limits of detection for immunoassays, however, they provide an explicit measure of the confidence in measuring a background signal. This estimation of confidence is easier to grasp and makes detection limits more meaningful than standard calculations. Henderson, R. A. *Clin. Chem.* 1993, 39, 929–935, hereby incorporated by reference. Therefore, we consider sample results positive if the observed signal lies outside of the 95% confidence interval (C.I.) for samples containing no analyte. The 99% C.I. was also determined and this more rigorous test is used for setting the limit of quantitation. Although a formal sensory panel should be convened for the determination of the lowest visually detectable color difference, signals near the calculated limit of detection were commonly rated as positive by laboratory workers. Table V displays these values and calibration curve equations for both the LIC and LIA formats. All values on the calibration curves fell very close to a true logarithmic trend, as evidenced by the high correlation coefficients and that the relative standard deviations for calibration points were approximately 6% for both assays.

Since the LIC C zone exhibited an extremely small signal range, the calibration curve for the LIC assay was read at the inversely proportional R zone. One possible reason for the lack of response at the LIC C zone could be the retention of liposomes by the membrane nonspecific binding sites resulting from the increased migration distance, as shown in FIG. 8A. Using the C zone, the LIC will give a positive result for amounts of Aroclor 1232 amounts greater than 0.4 nanomoles. The LIC format is not intended to be used quantitatively but the 99% C.I. is still listed for illustrative purposes. It can be seen in Table V that the LIA assay will detect PCBs at levels more than two orders of magnitude less than the LIC assay. Furthermore, the slope of the calibration curve indicates that the sensitivity of the LIA assay is approximately 2.6 times greater than the LIC assay. Associated with an increased sensitivity are increased signal and dynamic ranges for LIA. These ranges indicate the signal differences between zero and maximum analyte values.

TABLE V

Assay Characteristics

|  | LIC | LIA |
|---|---|---|
| Calibration Curve Equation[a] ($y = O.D.$; $x =$ nanomoles) | $y = -1.333 \log(x) + 7.799$ | $y = 3.484 \log(x) + 14.062$ |
| Correlation Coefficient ($r^2$) | 0.98 | 0.99 |
| Limit of Detection[b] | 0.37 | 0.0026 |
| Limit of Quantitation[c] | 0.48 | 0.0027 |
| Average % Relative STD | 5.70% | 6.20% |
| Max. Signal Range (O.D.) | 2.293 | 6.760 |
| Dynamic Range (nanomoles)[d] | 0.4–10 | 0.003–0.24 |
| Assay Time[e] | ca. 8 minutes | ca. 23 minutes |

[a]Calibration curve based on six data points spaced over the dynamic range.
[b]Indicates, in nanomoles/test, the upper limit of the 95% confidence interval for blank solutions.
[c]Indicates, in nanomoles/test, the upper limit of the 99% confidence interval for blank solutions.
[d]Range values indicate the span of O.D. signal (Signal Range) that resulted from the tested amounts of PCB (Dynamic Range). High dynamic range values resulted in the maximum signal attainable.
[e]Nitrocellulose migration requires ca. 8 minutes for both assays, however, LIA requires a 15-min incubation step.

Therefore, if very sensitive and more quantitative results are required, the LIA assay will be the method of choice. Other commercially available ELISA test provide standardized color cards for use if quantitation is desired and a similar scheme could be used for the LIA format. However, the advantage of the LIC format is that the entire assay takes less than 8 minutes because it does not require the aggregation step. The main advantage of LIC assays would come in situations when only threshold (e.g., tolerance level) measurements are required (>0.4 nanomoles/test) and when analysis time is critical. The need for both screening and quantitative immunoassay development for environmental contaminants has been noted by others, for example, in Van Vunakis, H. In Immunochemical methods for environmental analysis; Van Emon, J. M.; Mumma, R.O., Ed.; ACS: Washington, D.C., 1990; Vol. 442; 1–12, hereby incorporated by reference. The LIC and LIA formats based upon the detection of liposome migration described above and in co-pending Ser. No. 08/135,741 meet both of these needs.

The anti-PCB antibodies used in this study were expected to more readily bind to lower chlorinated mixtures due to the choice of a monochlorinated hapten for antibody production. Table VI shows the relative binding affinities of several Aroclors spanning the range of chlorine content that was present in commercial mixtures. The 2-chlorobiphenyl (2ClBP) which is analogous to our hapten was tested and assigned a value of 100% due to its similar structure to the hapten. Using the LIA assay, the percent reactivity was calculated by subtracting the background from all C zone greyscale readings and then comparing the various Aroclor mixtures to 2ClBP. All aroclors were tested at 100 ppb and could be detected using the polyclonal antibodies. However, as expected, the reactivity drops off at higher chlorination.

TABLE VI

LIA Determination of Aroclor Reactivity[a]

| PCB | % Chlorine | % Reactivity |
|---|---|---|
| 2-ClBP | 17.3 | 100.0 |
| Aroclor 1221 | 21.0 | 91.0 |
| Aroclor 1232 | 32.0 | 86.3 |
| Aroclor 1242 | 42.0 | 81.3 |
| Aroclor 1254 | 54.0 | 57.5 |
| Aroclor 1268 | 68.0 | 24.7 |

[a]% Reactivity = (C zone greyscale signal of Aroclor − background)/(C zone greyscale signal of 2ClBP − background)

A limited number of samples were obtained from a Superfund site in Tennessee. Equipment located on the site had been previously screened for PCBs by a private contractor who relied on a commercially available immunoassay wipe test as a primary screen and GC/MS as a confirmatory technique. Methanol (100%) was used as an extraction solvent for all wipe sheets. The limit of detection for the wipe test was 40 μg per 100 $cm^2$ for Aroclor 1232. Samples were measured by LIA analysis and compared to its calibration curve. In most of the tests, positive and negative samples were properly discriminated, although certain samples containing high amounts of diesel fuel caused an increase in liposome aggregation, thus yielding a false negative result. If these samples were diluted ten-fold into methanol, the PCBs could still be detected without the increased aggregation seen with the more concentrated samples. Some samples, that were determined to be negative by the commercial kit, gave signals significantly above the LIA limit of quantitation. The commercial kit could only detect PCBs at levels equivalent to 250 picomoles per test so the more sensitive LIA was detecting levels of contamination that would have been missed previously. Although more extensive studies are needed to investigate possible matrix effects, this liposome immunomigration technique has demonstrated the ability to detect PCBs in real-world samples.

Optimal amounts of extraction solvent, blocking reagents, antibody, and incubation time have been determined and used in the two complementary liposome-based immunomigration prototype devices for the rapid detection of PCBs described above. The liposome reagent proved to be stable in modest amounts of methanol and should be amenable to PCB detection in an environmental medium that is suitable for the extraction of PCBs using this solvent. This was confirmed by testing actual Superfund site samples that had been extracted in 100% methanol. It has been shown that the LIA assay can be used to measure the relative binding affinity between haptenated liposomes and anti-hapten antibodies, and this information can be used in the selection of antibodies on the basis of their affinities. Both of these devices are designed as single-use immunosensors which will reduce the problems of fouling and cross-contamination which are especially prevalent in field screening applications. All reagents are produced using standard techniques and are stable at room temperature. The devices are fabricated from commercially available nitrocellulose membranes. Furthermore, the LIA sensors do not contain an immobilized anti-analyte zone and thus can be used generically for any test for which a suitable incubation reaction has been developed.

The LIC device has been proposed as a rapid screening device for the detection of PCBs with amounts greater than 0.4 nanomoles per test. The LIA device, which is based on the size separation of liposome aggregates, is intended for more sensitive and quantitative measurements but requires an additional 15-minute incubation step. The LIA assay can detect PCB amounts down to 2.6 picomoles in ca. 23 minutes. The incubation step for the LIA assay was performed with only an initial manual mixing of reagents and with a single antibody reagent. This was done to maintain the simplicity of the prototype device. Others have noted that particle aggregation immunoassays often attain enhanced efficiency with the addition of a second anti-IgG antibody. See Monroe, D. *J. Liposome Res.* 1990, 1, 339–377, hereby incorporated by reference. However, many assays utilizing this technique exhibit rapid flocculation of aggregates. The liposome immunomigration devices presented here may be used for vertical migration from the incubation solution and, therefore, would be susceptible to losses due to particle settling. In order to ensure maximum aggregate delivery to the nitrocellulose sensor strips, we chose a less-aggressive aggregation technique that did not lead to flocculation during the 15 minute incubation step. Furthermore, because mechanical mixing of incubation solutions was observed to cause flocculation within 15 minutes, this approach was not used in the present study. Future experiments will be conducted to incorporate anti-IgG and mechanical stirring techniques with a delivery format that will allow the R zone to incorporate flocculated particles. This approach should help to decrease the incubation time of LIA and may eventually obviate the need for a LIC style format.

Table VII is a comparison of assay performance for two analytes (PCB and Alachlor) in the method of the invention. The data for Alachlor were obtained by procedures substantially as described in Examples 3–9 above. However, a greater (approximately 10-fold) concentration of PVP was employed in the blocking reagent, and pH-perturbed antibodies were employed.

169–181, each of which is hereby incorporated by reference. Although these assays have proven to be effective; their labeling technology lacks the signal amplification power and the diversity of labels available to liposome reagents. Liposome-based immunoassays provide an excellent means of delivering multiple labels and for instantaneously releasing ca. $10^7$ label molecules per binding event.

These examples are included to illustrate the practice of the invention. However, numerous variations and alternatives for the structure, components and use of the test device of the invention are possible. For example, a test device packaged as part of a commercial kit might include special holders for individual strips, in which openings are provided for sample application and optical readout, for example, as shown in FIG. 4. In such a configuration, the strips could be run in almost any orientation, e.g., lateral, instead of vertical flow.

In an alternative embodiment of the invention, a dual-strip test device as shown in FIG. 2 may be employed. In this design, after application of the protein zones, the strip is divided in two by removal of a very thin strip of nitrocellulose from the plastic backing, thereby providing two identical strips with a hydrophobic separation to prevent solution cross-talk. A tolerance level control is applied to the strip adjacent to the sample, and both are run simultaneously. This verifies the strip performance and provides a more quantitative interpretation of the strip results. As described above, multi-analyte assays may also be conducted using the test device and method of the invention.

The use of immunospecific liposome migration offers many advantages for the extra-laboratory detection of environmental contaminants. Devices utilizing this technique are

TABLE VII

| | Assay Performance | | | |
|---|---|---|---|---|
| | PCB Assay | | Alachlor Assay | |
| | LIC | LIA | LIC | LIA |
| Calibration Curve Equation[a] | y = −1.333 log(x) + 7.799 | y = 3.484 log(x) + 14.062 | y = 2.765 log(x) + 1.162 | y = 3.415 log(x) + 1.738 |
| Correlation Coefficient ($r^2$) | 0.98 | 0.99 | 0.965 | 0.981 |
| Limit of Detection[b] | 1000 ppb | 13 ppb | 6 ppb | 1 ppb |
| Average % Relative Std Dev | 5.7 | 6.2 | 3 | 3 |
| Dynamic Range[c] | 1–25 ppm | 13–1040 ppb | 6–100 ppb | 1–20 ppb |
| Assay Time[d] | 8 | 23 | 8 | 10 |

[a]Calibration curve based on six data points spaced over the dynamic range.
[b]Indicates, in ppb, the upper limit of the 95% confidence interval for blank solutions.
[c]Range values indicate the span of O.D. signal (Signal Range) that resulted from the tested amounts of PCB (Dynamic Range). High dynamic range values resulted in the maximum signal attainable.
[d]Nitrocellulose migration requires ca. 8 minutes for both assays, however, LIA requires an extra incubation step.

The assay methodology of the invention could potentially be applied to multianalyte environmental detection. Another major advantage of the use of a liposome reagent is their unique ability to entrap an almost unlimited range of colored, fluorescent, luminescent, and electroactive signal markers which can be used for multianalyte testing. Monroe, D. *J. Liposome Res.* 1990, 1, 339–377. Immunoassays which do not employ liposomes but which can simultaneously detect more than one analyte by incorporating separate labels or spatially resolving analyte binding have been described in Hayes, F. J.; Halsall, B.; Heineman, W. *Anal. Chem.* 1994, 66, 1860–1865; Parsons, R. G.; Kowal, R.; LeBlond, D.; Yue, V. T.; Neargarder, L.; Bond, L.; Garcia, D.; Slater, D.; Rogers, P. *Clin. Chem.* 1993, 39, 1899–1903; and Ekins, R.; Chu, F.; Biggart, E. *J. Clin. Immun.* 1990, 13, fast, easy to use, robust, and respond to the presence of analyte at low-parts-per billion concentrations. Two complementary prototype liposome-based immunomigration techniques have been developed for the detection of polychlorinated biphenyls (PCBs). The liposome immunocompetition (LIC) assay format measures the competitive reaction between analyte-tagged liposomes and the sample analyte for immobilized antibodies and can detect 0.4 nanomoles of PCB in less than 8 minutes. A more sensitive format, the liposome immunoaggregation (LIA) assay detects the inhibition of immunospecific liposome aggregation in solution and can detect 2.6 picomoles of PCB in less than 23 minutes. Laser diffraction particle sizing has been used to study LIA induced increases in liposome size over time and to determine optimal conditions for the application of this technique. Both formats utilize capillary action to transport liposome-containing solutions along strips of nitrocellulose. Measurement of color intensity is then carried out visually or with a desktop scanner.

The liposome immunocompetition (LIC) format has been previously investigated for detection of the herbicide, alachlor, as described in Siebert, T. A.; Reeves, S. G.; Durst, R. A. Anal. Chim. Acta 1993, 282, 297–305, and is now shown to be effective for the detection of PCBs. The present sensor format is based on the principle of immunoaggregation (liposome immunoaggregation or LIA) between anti-PCB antibodies and analyte-tagged liposomes. This second device represents a novel use of immunoaggregation for the detection of PCBs with a field-portable device. Both of these PCB sensors are fast, simple to use, and can be evaluated visually. They are made of easily obtainable plastic-backed nitrocellulose and all reagents can remain at room temperature for extended periods of time. Therefore, very little capital cost would be required to produce sensors with these components. Additionally, the immunomigration devices presented here require no change of solution and results are available within 8 minutes for the LIC assay and 23 minutes for the LIA assay.

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. A method for detecting or quantifying an analyte in a test sample, comprising:

providing a test device comprising an absorbent material, which absorbent material comprises:

a contact portion at or proximate to a first end of said absorbent material; and a measurement portion at a location on said absorbent material which is positioned away from the first end, said measurement portion having a receptor for a conjugate of an analyte analog and liposomes, wherein said receptor is non-diffusively bound to said measurement portion, and wherein said liposomes comprise a detectable marker;

combining a binding material specific for the analyte with the conjugate and the test sample to form a mixture;

incubating the mixture for a time sufficient to permit competition between any analyte present in the test sample and the conjugate for the binding material;

contacting the mixture with said contact portion of said absorbent material after said incubating;

allowing the mixture to migrate from the contact portion through said measurement portion of said absorbent material, wherein migration of aggregates of conjugate and binding material formed during said incubating is inhibited by said absorbent material;

detecting the presence or amount of said marker in said measurement portion of said absorbent material; and correlating the presence or amount of said marker in said measurement portion of said absorbent material with the presence or amount, respectively, of the analyte in the sample.

2. A method according to claim 1, wherein the analyte analog is either the analyte or a reactive analog of the analyte.

3. A method according to claim 1, wherein said contacting is carried out by inserting the contact portion of the absorbent material into the mixture.

4. A method according to claim 1, wherein the contact portion further comprises a wicking portion at the first end, said contacting being carried out by spotting the mixture onto the absorbent material in the contact portion outside of the wicking zone, and said allowing comprises inserting the wicking portion into a wicking reagent.

5. A method according to claim 1, wherein said correlating is used to determine the amount of analyte in the test sample and is carried out by comparing the amount of the marker in the measurement portion with one or more reference standards having known concentrations of the analyte for particular marker amounts to determine the analyte concentration in the test sample relative to the known concentrations.

6. A method according to claim 1, wherein the marker is a fluorescent dye, a visible dye, a bioluminescent material, a chemiluminescent material, a radioactive material, or an enzymatic substrate.

7. A method according to claim 6, wherein the marker is a fluorescent dye or a visible dye and said detecting is carried out by fluorometric or spectrophotometric measurement.

8. A method according to claim 6, wherein the marker is a visible dye and said detecting is carried out visually with the unaided eye.

9. A method according to claim 1, wherein the liposomes are prepared from one or more phospholipids, glycolipids, steroids, alkyl phosphates, or fatty acid esters.

10. A method according to claim 9, wherein the phospholipids are selected from the group consisting of lecithin, sphingomyelin, and dipalmitoyl, and the steroids are selected from the group consisting of cholesterol, chlorestanol, and lanosterol.

11. A method according to claim 1, wherein the liposomes are prepared from mixture comprising dipalmitoylphosphatidylcholine, cholesterol, and dipalmitoylphosphatidylglycerol.

12. A method according to claim 1, wherein the analyte is an antigen or hapten, and the binding material is an antibody recognizing the antigen or the hapten.

13. A method according to claim 1, wherein the analyte is alachlor, a PCB, dioxin, a hormone, a vitamin, a metabolite, or a pharmacological agent.

14. A method according to claim 1, wherein the receptor is capable of binding with either the liposomes or with a surface component of the liposomes.

15. A method according to claim 14, wherein the surface component and the receptor are each selected from the group consisting of avidin, biotin, and anti-biotin.

16. A method according to claim 1, wherein said detecting comprises lysing said liposomes to release said marker.

17. A method according to claim 1, wherein said absorbent material further comprises a region for accumulation of aggregates formed from said conjugate and said binding material, wherein said region for accumulation is positioned away from said measurement portion and either between said measurement portion and said contact portion, or in said contact portion.

18. A method according to claim 1, wherein said marker is encapsulated within said liposomes.

* * * * *